(12) United States Patent
Kohgo

(10) Patent No.: US 12,173,023 B2
(45) Date of Patent: Dec. 24, 2024

(54) CROSSLINKED NUCLEOSIDE INTERMEDIATE CRYSTAL AND METHOD FOR PRODUCING SAME, AND METHOD FOR PRODUCING CROSSLINKED NUCLEOSIDE AMIDITE

(71) Applicant: Yamasa Corporation, Choshi (JP)

(72) Inventor: Satoru Kohgo, Chiba (JP)

(73) Assignee: YAMASA CORPORATION, Chiba (JP)

( * ) Notice: Subject to any disclaimer, the term of this patent is extended or adjusted under 35 U.S.C. 154(b) by 652 days.

(21) Appl. No.: 17/608,780

(22) PCT Filed: Jun. 18, 2020

(86) PCT No.: PCT/JP2020/024037
§ 371 (c)(1),
(2) Date: Nov. 4, 2021

(87) PCT Pub. No.: WO2020/256084
PCT Pub. Date: Dec. 24, 2020

(65) Prior Publication Data
US 2022/0315617 A1    Oct. 6, 2022

(30) Foreign Application Priority Data

Jun. 19, 2019 (JP) .................................. 2019-113372

(51) Int. Cl.
| | |
|---|---|
| C07H 1/00 | (2006.01) |
| C07H 15/18 | (2006.01) |
| C07H 19/06 | (2006.01) |
| C07H 19/16 | (2006.01) |

(52) U.S. Cl.
CPC ............... *C07H 1/00* (2013.01); *C07H 15/18* (2013.01); *C07H 19/06* (2013.01); *C07H 19/16* (2013.01)

(58) Field of Classification Search
None
See application file for complete search history.

(56) References Cited

U.S. PATENT DOCUMENTS

| | | | |
|---|---|---|---|
| 7,034,133 B2 * | 4/2006 | Wengel | C07H 21/00 536/23.1 |
| 2002/0068708 A1 | 6/2002 | Wengel et al. | |
| 2003/0105309 A1 | 6/2003 | Imanishi et al. | |

FOREIGN PATENT DOCUMENTS

| | | |
|---|---|---|
| EP | 1152009 A1 | 11/2001 |
| JP | 10-304889 A | 11/1998 |
| JP | 2002-521310 A | 7/2002 |

OTHER PUBLICATIONS

Seth et al., Synthesis and biophysical evaluation of 2',4'-constrained 2'O-methoxyethyl and 2',4'-constrained 2'O-ethyl nucleic acid analogues. J Org Chem. Mar. 5, 2010;75(5):1569-81.
European communication dated Aug. 25, 2022 in corresponding European patent application No. 20827632.9.
International Preliminary Report on Patentability issued Dec. 30, 2021 in corresponding PCT application No. PCT/JP2020/024037.
International Search Report and Written Opinion mailed Jul. 21, 2020 in corresponding PCT application No. PCT/JP2020/024037.
Fukuyama, "Development of Efficient Synthetic Methods for C4-Tetrasubstituted Nucleoside Derivatives with Pharmacological Activities", Tohoku University Doctoral Dissertation, Tohoku University, degree conferment No. 11301 No. 17068, Mar. 2016.
Koshkin et al., "A Simplified and Efficient Route to 2'-O, 4'-C-Methylene-Linked Bicyclic Ribonucleosides (Locked Nucleic Acid)", Journal of Organic Chemistry, vol. 66, pp. 8504-8512, 2001.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", Tetrahedron, vol. 54, pp. 3607-3630, 1998.
Waga et al., "Synthesis of 4'-C-Methylnucleosides", Bioscience, Biotechnology, and Biochemistry, vol. 57, pp. 1433-1438, 1993.
Caira, "Crystalline Polymorphism of Organic Compounds", Topics in Current Chemistry, vol. 198, pp. 163-208, Jan. 1998.
Indian communication dated Sep. 21, 2023 in corresponding Indian patent application No. 202127057115.

* cited by examiner

*Primary Examiner* — Patrick T Lewis
(74) *Attorney, Agent, or Firm* — NIELDS, LEMACK & FRAME, LLC

(57) ABSTRACT

A crystal of a compound represented by the following formula 5:

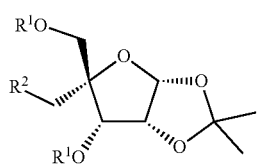

in which $R^1$ represents a protecting group for a hydroxyl group, and $R^2$ represents a leaving group.

8 Claims, 5 Drawing Sheets

CROSSLINKED NUCLEOSIDE INTERMEDIATE CRYSTAL AND METHOD FOR PRODUCING SAME, AND METHOD FOR PRODUCING CROSSLINKED NUCLEOSIDE AMIDITE

FIELD OF THE INVENTION

The present disclosure relates to a crosslinked nucleoside intermediate crystal and a method for producing the same, as well as a method for producing a crosslinked nucleoside amidite.

BACKGROUND OF THE INVENTION

There are methods for treating diseases with nucleic acid drugs, including antisense, anti-gene, aptamer, and siRNA methods.

In general, a furanose ring of a nucleoside sugar moiety presents a distorted conformation called an N-type or S-type, rather than a planar structure, and is biased to a particular conformation by substituents on the ring. For example, in the case of a ribonucleoside having a hydroxyl group at the position 2', the N-type conformation is dominant.

Imanishi et al. succeeded in forcibly fixing the conformation of the nucleoside to the N-type by crosslinking 4' and 2' hydroxyl groups of the nucleoside sugar moiety. As a result, it was revealed that LNA (Locked Nucleic Acid) containing the crosslinked nucleoside formed extremely stable double stranded chains with nucleic acids having complementary sequences (see Patent Literature 1).

The above properties and the like have led to increased expectations for LNA as a material for nucleic acid medicines in recent years.

As examples of synthesis methods for crosslinked nucleosides, methods of using nucleosides as raw materials (Patent Literature 1) and sugars as starting materials (Patent Literature 2, Non-Patent Literature 1, Non-Patent Literature 2) are known in the art.

Among the existing synthetic methods for crosslinked nucleosides, the following synthetic method has been proposed by Tohoku University as one of good methods (Non-Patent Literature 3).

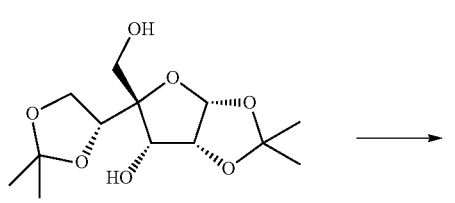

a

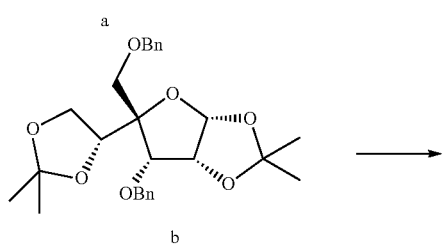

b

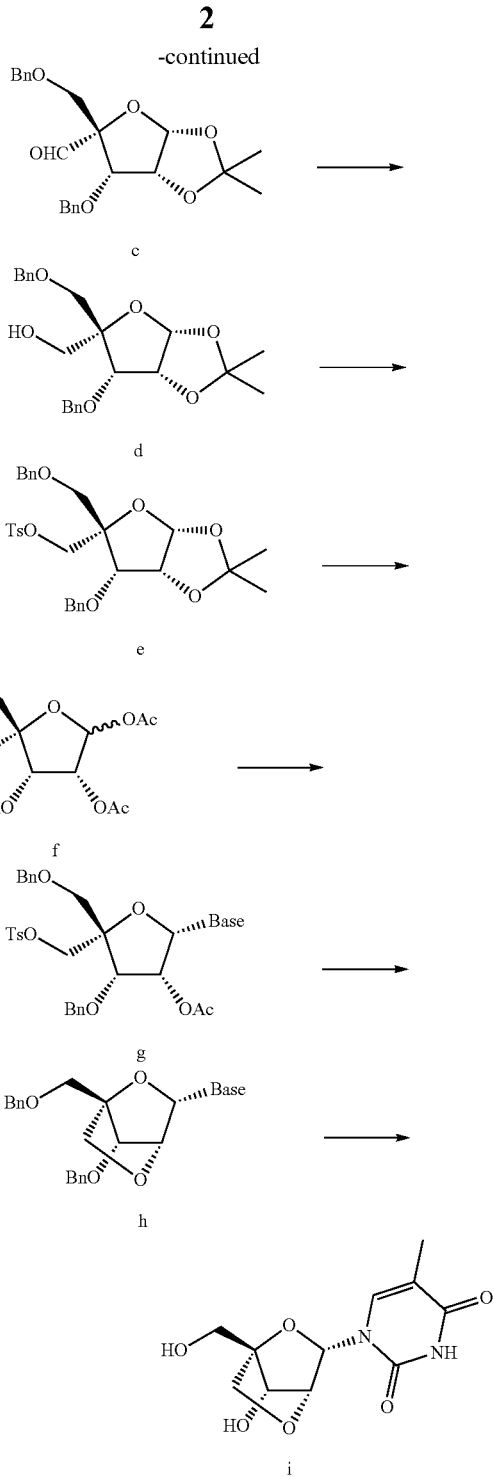

CITATION LIST

Patent Literatures

[Patent Literature 1] Japanese Patent Application Publication No. H10-304889 A

[Patent Literature 2] Japanese Patent Application Publication No. 2002-521310 A

Non-Patent Literatures

[Non-Patent Literature 1] J. Org. Chem. 2001, 66, 8504-8512
[Non-Patent Literature 2] Tetrahedron 1998, 54, 3607-3630
[Non-Patent Literature 3] Ph. D Thesis in Tohoku University (11301A, No. 17068, 2016)

SUMMARY OF THE INVENTION

Problem to be Solved by the Invention

A purpose of each of the existing synthesis methods for crosslinked nucleosides (e.g., those described in Patent Literatures 1 and 2, and Non-Patent Literature 2) is to synthesize a crosslinked nucleoside amidite by a series of steps. Therefore, the stability and storage of reaction intermediates (hereinafter referred to as "crosslinked nucleoside intermediates") have not been studied.

However, the present inventors have conducted a study, and found a problem that the existing synthesis methods for crosslinked nucleosides must be through a relatively unstable reaction intermediate. The industrial production of the crosslinked nucleoside requires synthesis of a plurality of crosslinked nucleosides from specific reaction intermediates as needed, and ideally, it is desirable to be able to stably store the specific reaction intermediates.

In other words, an object of the present disclosure is to provide a crystal of a compound that can be used as a crosslinked nucleoside intermediate capable of being stably stored for a long period of time, and a method for producing the same. Also, an object of the present disclosure is to provide a method for producing a crosslinked nucleoside amidite using the crystal of the compound.

Methods for Solving the Problem

As a result of intensive studies to solve the above problems, the present inventors have found that a compound having specific substituents can be easily crystallized and stably stored as a crosslinked nucleoside intermediate in the form of the crystal.

Thus, the present disclosure relates to inventions as specified below:

[1]
A crystal of a compound represented by the following formula 5:

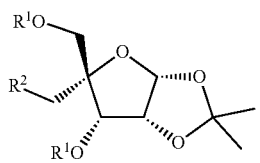

5

In the above formula, $R^1$ represents a protecting group for a hydroxyl group, and $R^2$ represents a leaving group.

[2]
The crystal according to [1], wherein the crystal shows peaks at 5.9±0.3, 11.4±0.6, 11.8±0.6, 13.2±0.7, 16.2±0.8, 17.2±0.9, 18.5±0.9, 19.5±1.0, 19.7±1.0, 20.1±1.0, 20.4±1.0, 21.4±1.1, 22.0±1.1, 23.0±1.2, 24.1±1.2, 24.3±1.2, 26.4±1.3, and 29.9±1.5(°) as a diffraction angle (2θ) in powder X-ray analysis.

[3]
The crystal according to [1] or [2], wherein the crystal shows an endothermic peak at 124° C. as measured by a thermogravimetry/differential thermal analysis (TG/DTA) apparatus.

[4]
The crystal according to any one of [1] to [3], wherein the compound represented by the formula 5 is a crosslinked nucleoside intermediate.

[5]
A method for producing a crystal of a compound represented by a formula 5, the method comprising the following steps 1 to 5:

step 1: protecting hydroxyl groups of a compound represented by formula 1 to obtain a compound represented by formula 2;

step 2: converting a dimethyldioxolanyl group at position 4 of a compound represented by formula 2 to an aldehyde group to obtain a compound represented by formula 3;

step 3: reducing the compound represented by the formula 3 to convert the aldehyde group at the position 4 to a hydroxyl group to obtain a compound represented by formula 4;

step 4: converting the hydroxyl group at the position 4 of the compound represented by the formula 4 to a leaving group to obtain a compound represented by formula 5; and step 5: crystallizing the compound represented by the formula 5 from a crystallization solvent to obtain the crystal of the compound represented by the formula 5.

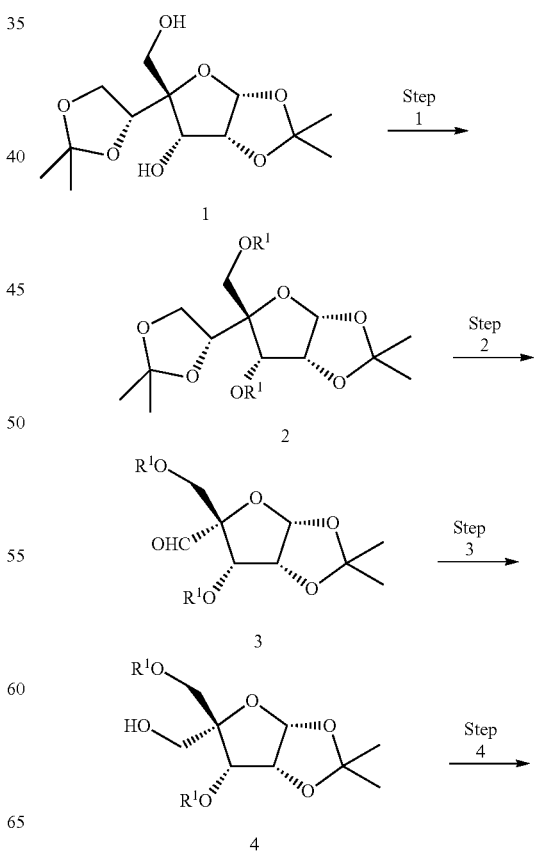

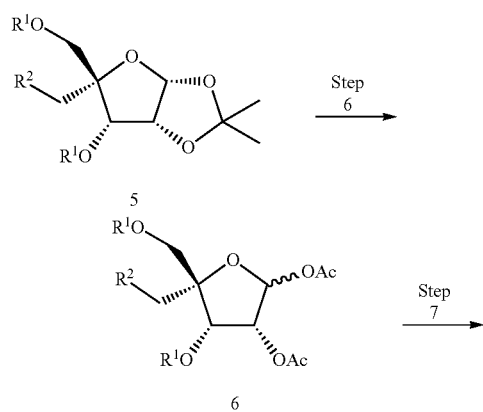

In the above formula, $R^1$ represents a protecting group for a hydroxyl group, and $R^2$ represents a leaving group.

[6]

The method for producing the crystal according to [5], further comprising a crystallization step between the step 2 and the step 3.

[7]

The method for producing the crystal according to [5] or [6], wherein the compound represented by the formula 5 is a crosslinked nucleoside intermediate.

[8]

A method for producing a crosslinked nucleoside amidite, the method comprising the following steps:

step 6: suspending the crystal of the compound represented by the formula 5 obtained by the method according to any one of [5] to [7] in a solvent, and then converting isopropylidene groups of the compound to acetyl groups to obtain a compound represented by formula 6;

step 7: condensing the compound represented by the formula 6 with a silylated base to obtain a compound represented by formula 7;

step 8: removing protecting groups of the compound represented by the formula 7 while at the same time performing a cyclization reaction to obtain a compound represented by formula 8;

step 9: removing the protecting groups for the hydroxyl groups of the compound represented by the formula 8 to obtain a compound represented by formula 9; and step 10: optionally introducing a protecting group into the amino group on the base moiety of the compound represented by the formula 9 to obtain a compound represented by formula 10.

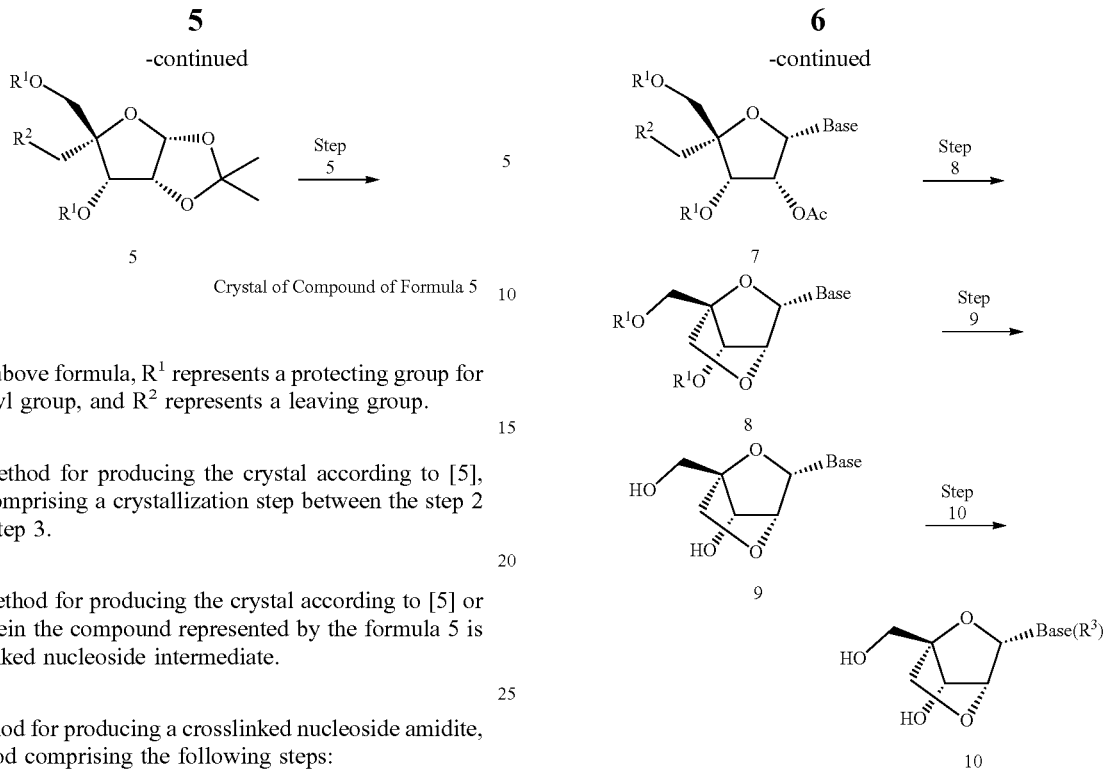

in which $R^1$ represents a protecting group for the hydroxyl group, $R^2$ represents a leaving group, and $R^3$ represents a hydrogen atom or an amino-protecting group.

Effects of Invention

According to the present disclosure, it is possible to provide a crystal of a compound that can be used as a crosslinked nucleoside intermediate capable of being stably stored for a long period of time, and a method for producing the same. Also, according to the present disclosure, it is possible to provide a method for producing a crosslinked nucleoside amidite using the crystal of the compound.

DETAILED DESCRIPTION OF THE INVENTION

Hereinafter, embodiments according to the present invention will be specifically described. It is to understand that the present invention is not limited to the following embodiments, and various modifications and improvements, which will be within the scope of the present invention, may be made based on ordinary knowledge of a person skilled in the art, without departing from the spirit of the present invention.

The present disclosure relates to a crystal of a compound represented by formula 5 below, as described above.

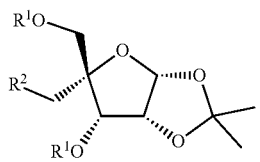

In the above formula, $R^1$ represents a protecting group for a hydroxyl group, and $R^2$ represents a leaving group.

Figure 1:
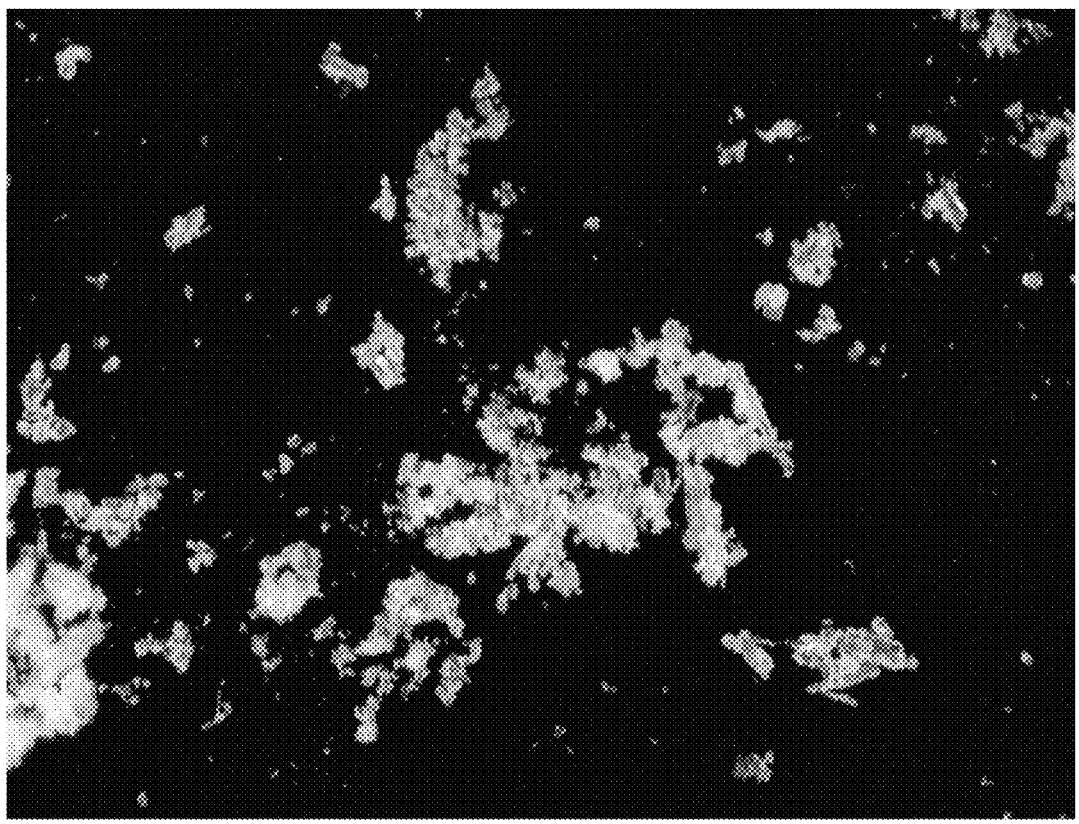
FIG. 1 shows a photograph of a crystal of a compound represented by formula 5.

The crystal according to the present disclosure has an appearance as shown in FIG. 1, when observed with a microscope as described below in Examples.

The crystal according to the present disclosure has characteristic peaks in powder X-ray analysis.

The powder X-ray diffraction used herein is carried out under the following conditions:
[X-ray analysis apparatus] X' Pert PRO MPD (from Spectris);
[Target] Cu;
[X-ray tube current] 40 mA;
[X-ray tube voltage] 45 kV; and
[Scanning range] 2θ=4.0 to 40°.

The analysis of the crystal according to the present disclosure by the powder X-ray diffractometer under the conditions as described above shows characteristic peaks near the diffraction angle (2θ) as shown below in Table 1 (see FIG. 2), as described below in Examples.

TABLE 1

| No. | Pos. [°2Th.] | d Value [Å] | NET Intensity [cts] | Relative Intensity [%] |
|---|---|---|---|---|
| 1 | 5.9165 | 14.93835 | 2502.83 | 25.18 |
| 2 | 10.1471 | 8.71762 | 625.56 | 6.29 |
| 3 | 11.3691 | 7.78318 | 2243.71 | 22.57 |
| 4 | 11.8382 | 7.47580 | 7576.93 | 76.22 |
| 5 | 13.1577 | 6.72893 | 3047.28 | 30.66 |
| 6 | 15.3195 | 5.78389 | 610.48 | 6.14 |
| 7 | 16.1935 | 5.47364 | 3654.28 | 36.76 |
| 8 | 17.1773 | 5.16231 | 1409.99 | 14.18 |
| 9 | 17.7460 | 4.99814 | 478.93 | 4.82 |
| 10 | 18.4906 | 4.79851 | 4680.94 | 47.09 |
| 11 | 19.4686 | 4.55962 | 9940.27 | 100.00 |
| 12 | 19.7004 | 4.50649 | 6210.24 | 62.48 |
| 13 | 29.0967 | 4.41850 | 4495.28 | 45.22 |
| 14 | 20.3630 | 4.36133 | 2937.43 | 29.55 |
| 15 | 21.4153 | 4.14933 | 5525.77 | 55.59 |
| 16 | 21.9978 | 4.04075 | 3202.83 | 32.22 |
| 17 | 22.9853 | 3.86935 | 7071.51 | 71.14 |
| 18 | 24.0829 | 3.69542 | 2077.87 | 20.90 |
| 19 | 24.3163 | 3.66048 | 2619.89 | 26.36 |
| 20 | 25.7510 | 3.45970 | 702.44 | 7.07 |
| 21 | 25.9498 | 3.43365 | 600.86 | 6.04 |
| 22 | 26.4303 | 3.37230 | 1359.33 | 13.67 |
| 23 | 27.9228 | 3.19535 | 787.09 | 7.92 |
| 24 | 28.5826 | 3.12308 | 596.98 | 6.01 |
| 25 | 28.8891 | 3.09064 | 811.35 | 8.16 |
| 26 | 29.2447 | 3.05386 | 958.89 | 9.65 |
| 27 | 29.8553 | 2.99278 | 995.33 | 10.01 |
| 28 | 30.7443 | 2.90824 | 420.84 | 4.23 |
| 29 | 31.7594 | 2.81756 | 287.01 | 2.89 |

TABLE 1-continued

| No. | Pos. [°2Th.] | d Value [Å] | NET Intensity [cts] | Relative Intensity [%] |
|---|---|---|---|---|
| 30 | 32.1622 | 2.78319 | 612.03 | 6.16 |
| 31 | 32.7859 | 2.73165 | 320.05 | 3.22 |
| 32 | 33.3645 | 2.68560 | 249.63 | 2.51 |
| 33 | 34.4102 | 2.60634 | 761.54 | 7.66 |
| 34 | 36.0061 | 2.49439 | 579.68 | 5.83 |
| 35 | 36.9022 | 2.43586 | 691.66 | 6.96 |
| 36 | 38.2233 | 2.35465 | 315.45 | 3.17 |

When the crystal according to the present disclosure is analyzed by the powder X-ray diffractometer under the above conditions, the peaks having relative intensities of 10% or more are shown at 5.9, 11.4, 11.8, 13.2, 16.2, 17.2, 18.5, 19.5, 19.7, 20.1, 20.4, 21.4, 22.0, 23.0, 24.1, 24.3, 26.4, and 29.9 (°).

In general, the diffraction angle (2θ) in the powder X-ray diffraction may include an error range of less than 5%. Therefore, in addition to crystals in which the peak diffraction angles in the powder X-ray diffraction match exactly, crystals in which the peak diffraction angles match in an error of less than 5% are also included in the crystal according to the present disclosure. In the powder X-ray diffraction, for example, the diffraction angles (2θ) of peaks each having a relative intensity of 10% or more show 5.9±0.3, 11.4±0.6, 11.8±0.6, 13.2±0.7, 16.2±0.8, 17.2±0.9, 18.5±0.9, 19.5±1.0, 19.7±1.0, 20.1±1.0, 20.4±1.0, 21.4±1.1, 22.0±1.1, 23.0±1.2, 24.1±1.2, 24.3±1.2, 26.4±1.3, and 29.9±1.5 (°).

The crystal of the compound represented by formula 5 according to the present disclosure has an endothermic peak at 124° C. when it is analyzed by a thermogravimetry/differential thermal analysis (TG/DTA) apparatus (a temperature rising rate of 5° C./min), as described below in Examples (see FIG. 3).

The thermogravimetry/differential thermal analysis (TG/DTA) used herein is carried out under the following condition:
[Equipment used] Thermal analyzer STA 7200 (Hitachi High-Tech Science Corporation); and
[Conditions for Measurement] The temperature is increased by 5° C. per minute in the range of from 30 to 190° C., and a change of heat quantity of a sample is measured. Aluminum oxide is used as a reference.

The crystal of the compound represented by the formula 5 according to the present disclosure can be stably stored for a long period of time at room temperature. The stability of the compound for the long period of time can be evaluated by conducting an accelerated test under the conditions as described below in Examples.

Figure 4:
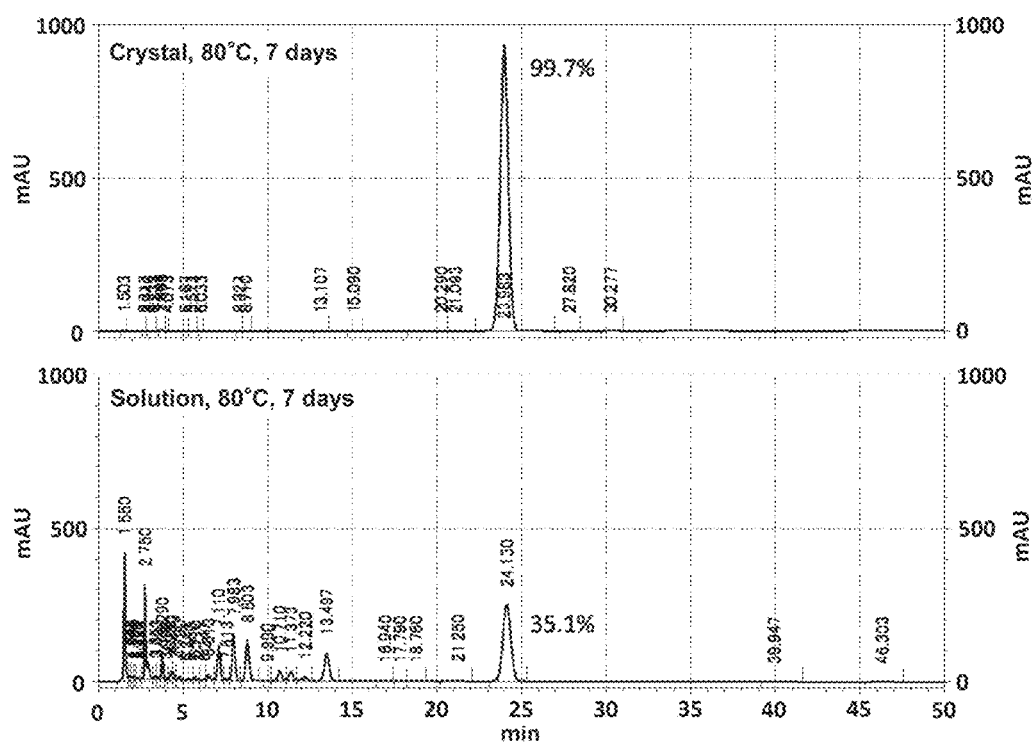
FIG. 4 shows results of an accelerated test for a crystal of a compound represented by formula 5.

In this case, the crystal according to the present disclosure exhibits an HPLC purity of 90% or more, and preferably 95% or more, and even more preferably 98% or more, and still more preferably 99% or more, and even more preferably 99.5% or more, even after the accelerated test (see FIG. 4).

The present disclosure also relates to a method for producing the crystal of the compound represented by the formula 5, which includes the following steps 1 to 5:
step 1: protecting hydroxyl groups of a compound represented by formula 1 to obtain a compound represented by formula 2;
step 2: converting a dimethyldioxolanyl group at position 4 of the compound represented by the formula 2 to an aldehyde group to obtain a compound represented by formula 3;

step 3: reducing the compound represented by the formula 3 to convert the aldehyde group at the position 4 to a hydroxyl group to obtain a compound represented by formula 4;

step 4: converting the hydroxyl group at the position 4 of the compound represented by the formula 4 to a leaving group to obtain a compound represented by formula 5; and step 5: crystallizing the compound represented by the formula 5 from a crystallization solvent to obtain a crystal of the compound represented by the formula 5.

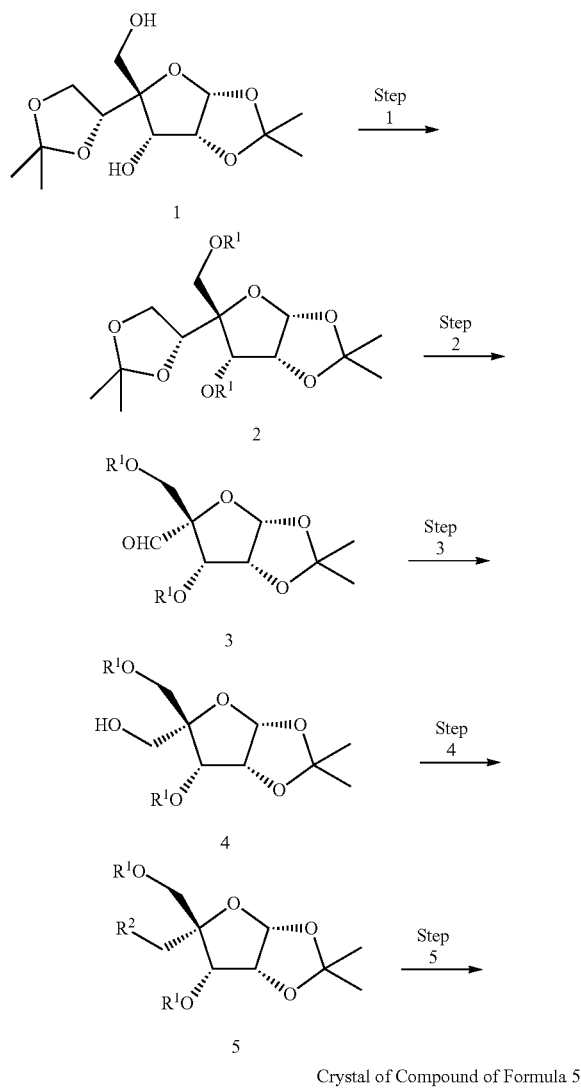

In the above formula, $R^1$ represents a protecting group for a hydroxyl group, and $R^2$ represents a leaving group.

The synthetic method that uses the compound represented by the formula 1 as a starting material and includes the steps 1-5 is described in detail below.

The compound represented by the formula 2 can be obtained by protecting the hydroxyl groups at positions 3 and 5 of the compound represented by the formula 1 with 4-substituted benzyl groups. Among the 4-substituted benzyl groups, 4-halobenzyl groups such as a 4-fluorobenzyl group, a 4-chlorobenzyl group, a 4-bromobenzyl group, and a 4-iodobenzyl group, and a 4-nitrobenzyl group are prefer-able, because they allow the compound represented by the formula 5 according to the present disclosure to exhibit good crystallinity. Among them, the 4-chlorobenzyl group, 4-bromobenzyl group, 4-iodobenzyl group, and 4-nitrobenzyl group are preferable in terms of higher crystallinity of the compound represented by the formula 5 according to the present disclosure, and the 4-bromobenzyl group is more preferable in terms of availability and cost.

The introduction of the 4-substituted benzyl groups into the compound represented by the formula 1 may be carried out according to a known method. For example, to introduce the 4-bromobenzyl groups, the compound is treated with NaH in DMF at 0° C. for 15 minutes to 3 hours, and then allowed to react with 4-bromobenzyl bromide at room temperature for 1 hour to 24 hours. Alternatively, it is possible to use Schotten-Baumann type condition which is a combination of a sodium hydroxide solution, a potassium hydroxide solution, and a halogen-based solvent such as dichloromethane and chloroform, and an ether solvent such as tetrahydrofuran and 2-methyltetrahydrofuran as organic solvents. Further, various methods for introducing protective groups described in "Protective Groups in ORGANIC SYNTHESIS" may also be used.

The compound represented by the formula 1 is known in the art, which may use a commercially available product or synthesized by a known method (e.g., J. Org. Chem. 2015, 80, 5337-5343).

The step 2 is a step of converting the dimethyldioxolanyl group at the positon 4 of the compound represented by the formula 2 to the aldehyde group to obtain the compound represented by the formula 3.

In this step, a deprotecting agent is added to deprotect the dimethyldioxolanyl group at the position 4 to form a diol. The deprotecting agent that can be used herein includes acetic acid, trifluoroacetic acid, hydrochloric acid, sulfuric acid, iodine, and the like. Among them, acetic acid is preferable due to its ease of availability and handling.

An amount of the deprotecting agent added may be appropriately set depending on the type of deprotecting agent. In the case of acetic acid, for example, a solvent amount may preferably be used.

Further, it is preferable to use water as an auxiliary solvent because of easy purification by crystallization, as described below. A ratio of the deprotecting agent to the auxiliary solvent is preferably about 10:1 to 1:1 on a volume basis, and more preferably 2:1.

In this step, an oxidizing agent is used to oxidatively cleave the diol resulting from the deprotection of the dimethyldioxolanyl group at the position 4 to convert the diol to the aldehyde group. The available oxidizing agents include periodate salts such as sodium periodate and potassium periodate, and lead tetraacetate. Among them, sodium periodate is preferably used in an amount of 1 to 10 molar equivalents relative to the diol in terms of cost and toxicity. An amount of the oxidizing agent used is preferably 1 to 2 mole equivalents.

In the step 2, an additive may be used in order to increase the reactivity of the oxidizing agent. Examples of the additive include iodine and the like.

Among the combinations of the reaction conditions in the step 2 as described above, it is preferable to use acetic acid as the deprotecting agent, water as the solvent, and sodium periodate as the oxidant.

When these conditions are used, the reaction can be carried out at 0 to 100° C. A reaction temperature of 50 to 80° C. is particularly preferable. The reaction can be carried out under the above conditions for 1 to 24 hours.

The combination is suitable for industrial production, because there is no excess iodine or the like in the reaction system and the solvent can be easily discarded after the reaction. Further, the use of the compound represented by the formula 1 can provide the compound represented by the formula 3 with a high yield of 70 to 90% or more by crystallization without using any purification means such as chromatography.

The step 3 is a reducing the compound represented by the formula 3 to convert the aldehyde group at the position 4 to a hydroxyl group to obtain the compound represented by the formula 4.

This step requires addition of a reducing agent. Examples of the reducing agent that can be used herein include, but not limited to, sodium borohydride, lithium aluminum hydride, borane derivatives and the like, catalytic reduction, and the like. Among them, sodium borohydride is preferably used in terms of cost and safety. An amount of the reducing agent added can optionally be adjusted depending on the type of the reducing agent. For example, in the case of sodium borohydride, it may preferably be used in an amount of 0.25 to 10 molar equivalents, more preferably 0.25 to 2 molar equivalents, relative to the compound represented by the formula 3. Under the above conditions, the reaction can be carried out at −30 to 50° C., more preferably at −10 to 25° C., for 10 to 120 minutes.

The solvent in this step can be used as needed according to the type of the reducing agent, and the like. For example, it may use water as an aqueous solvent; an alcohol solvent such as methanol and ethanol, tetrahydrofuran, 2-methyltetrahydrofuran, 4-methyltetrahydropyran, as an organic solvent; and combinations of thereof.

The step 4 is a step of converting the hydroxyl group at the position 4 of the compound represented by the formula 4 to a leaving group to obtain the compound represented by the formula 5.

Although the leaving group introduced in this step is not particularly limited, substituents each having high reactivity in nucleophilic substitution reaction are preferable in order to carry out the crosslinking reaction efficiently. Examples of such substituents include 4-toluenesulfonyloxy groups, methanesulfonyloxy groups, chloromethanesulfonyloxy groups, trifluoromethanesulfonyloxy groups, and halogeno groups. Among them, the 4-toluenesulfonyloxy group is preferred because its leaving group introducing reagent is easily availability and inexpensive.

For the solvent used in this step, an organic solvent or a combination of water and the organic solvent can be selected depending on the type of the leaving group to be introduced. More particularly, it is possible to utilize a combination of a halogenated solvent such as pyridine, dichloromethane and chloroform, and an organic base such as triethylamine, as an organic solvent, or a Schotten-Baumann type condition which is a combination of water/an organic base such as triethylamine, an aqueous sodium hydroxide solution, an aqueous potassium hydroxide solution, as an aqueous solvent, and a halogen solvent such as dichloromethane and chloroform, and an ether solvent such as tetrahydrofuran and 2-methyltetrahydrofuran, as an organic solvent. Among them, one of pyridine, the aqueous sodium hydroxide solution/tetrahydrofuran, and the aqueous sodium hydroxide solution/2-methyltetrahydrofuran is preferred in terms of toxicity and cost. An amount of the reagent used to introduce the leaving group can be selected depending on the types of substituted leaving groups and solvents. For example, when 4-toluenesulfonyl chloride is used as the leaving group and pyridine is used as the solvent, they are preferably used in the amount of 1 to 10 molar equivalents, more preferably 1 to 2 molar equivalents, relative to the compound represented by the formula 3. The reaction can be carried out under the above conditions at −10 to 100° C., more preferably at 0 to 60° C., for 1 to 24 hours.

The step 5 is a step of performing a post-treatment operation on the synthetic reaction solution of the compound represented by the formula 5 to obtain the crystal of the compound represented by the formula 5. Examples of a crystallizing solvent for the compound represented by the formula 5 include an alcohol solvent such as ethanol, and a combination of various good solvents and poor solvents. Examples of good solvents include ethyl acetate, tetrahydrofuran, pyridine, chloroform, acetonitrile, acetone, and derivatives thereof. Examples of the poor solvent include hexane, alcohol, water, and derivatives thereof.

In each of the above steps, isolation/purification operations may be carried out at the end of the step, if necessary, or may not be carried out. Examples of the method for isolation/purification include various chromatography such as ion exchange, and adsorption, and crystallization. The crystallization is preferable because the compound obtained by the synthetic method according to the present disclosure is highly crystalline.

In particular, the compound represented by the formula 3 is preferably purified by the crystallization. That is, it is preferable to further include a crystallization step between the steps 2 and 3. When purifying the compound by the crystallization, the solvent for the reaction is preferably acetic acid/water. At this time, as the reaction progresses, the crystal of the compound represented by the formula 3 are precipitated.

In this case, the target compound is precipitated as crystals, as the reaction progresses, so that it is possible to prevent the formation of by-products due to decomposition by an excessive reaction, which will increase a purification effect. Therefore, in the step 2, by-production and contamination of impurities can be suppressed without performing any complicated purification operation by chromatography (see FIG. 5(a)).

Figure 5:
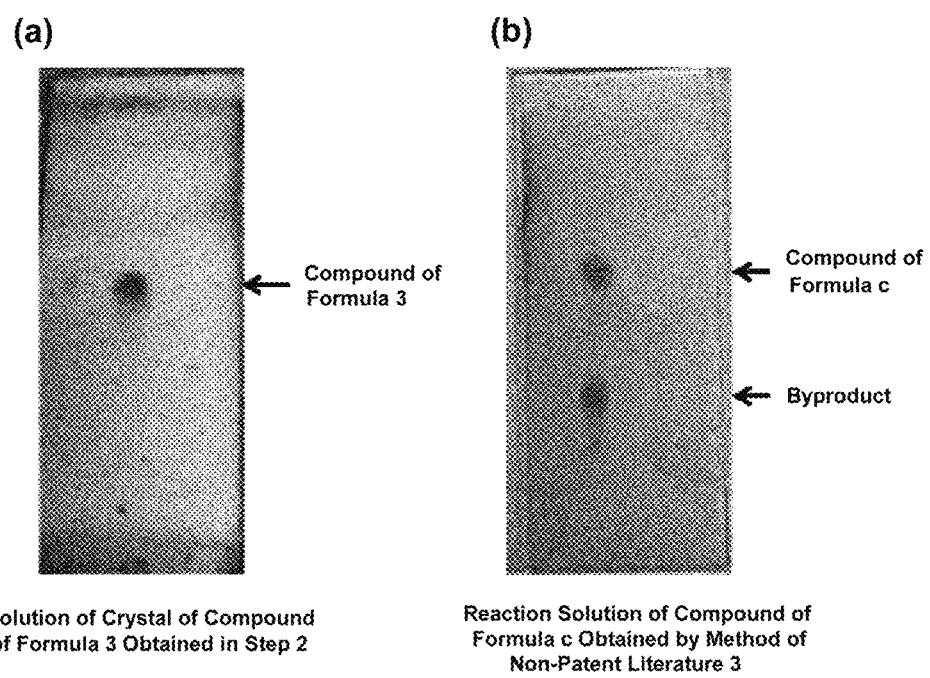
FIG. 5 shows (a): results of TLC analysis for a dissolved solution of a crystal of a compound represented by formula 3, obtained in step 2; and (b) results of TLC analysis for a reaction solution of a compound represented by formula c, obtained under the conditions as described in Non-Patent Literature 3.

On the other hand, when the compound represented by the formula c is synthesized from the compound represented by the formula b as described above using the method described in Non-Patent Literature 3, more impurities will be formed as by-products (see FIG. 5(a)). Further, since the compound represented by the formula c is amorphous, a complicated purification operation by chromatography is required for carrying out the purification.

The crystal of the compound represented by the formula 5 according to the present disclosure can be used as a crosslinked nucleoside intermediate, because the crystal can be stably stored for a long period of time. The crystal is also suitable for industrial production because it does not require any purification step by chromatography.

The crystal of the compound represented by the formula 5 according to the present disclosure can be used to synthesize a crosslinked nucleoside by steps 6-10 as described below, according to known descriptions in Non-Patent Literature 2 or the like:

step 6: suspending the crystal of the compound represented by the formula 5 obtained by the method according to any one of [5] to [7] in a solvent, and then converting isopropylidene groups of the compound to acetyl groups to obtain a compound represented by formula 6;

step 7: condensing the compound represented by the formula 6 with a silylated base to obtain a compound represented by formula 7;

step 8: removing protecting groups of the compound represented by the formula 7 while at the same time performing a cyclization reaction to obtain a compound represented by formula 8;

step 9: removing the protecting groups for the hydroxyl groups of the compound represented by the formula 8 to obtain a compound represented by formula 9; and step 10: optionally introducing a protecting group into the amino group on the base moiety of the compound represented by the formula 9 to obtain a compound represented by formula 10.

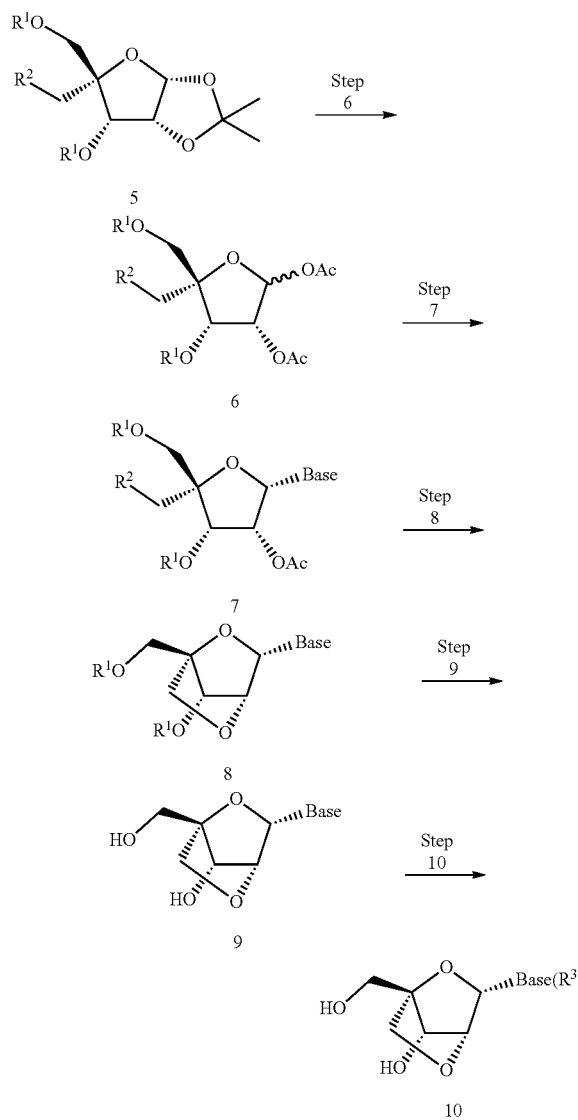

In the above formula, $R^1$ represents a protecting group for the hydroxyl group, $R^2$ represents a leaving group, and $R^3$ represents a hydrogen atom or an amino-protecting group.

The "Base" in the above formula may be a base such as 2-thiouracil, 5-propynyluracil, 5-propynylcytosine, 2,6-diaminopurine, in addition to thymine, uracil, adenine, cytosine, 5-methylcytosine, and guanine. Further, during the step, these bases can further undergo a chemical reaction to be converted to other bases.

The amino groups on these bases may be protected by acyl groups such as acetyl, phenoxyacetyl, benzoyl, and isobutyryl groups, or protecting groups such as a dimethylformamidino group.

Furthermore, it will be easily understood by a person skilled in the art that the above crosslinked nucleoside can be converted to the corresponding crosslinked nucleoside amidite, as described in Non-Patent Literature 2 and the like.

The method for producing the crosslinked nucleoside according to the present disclosure uses the crystal of the compound represented by the formula 5, which can be stably stored, as the crosslinked nucleoside intermediate, so that a variety of crosslinked nucleosides can be produced as required.

EXAMPLES

Examples will be described below, but the present invention is not limited to the Examples.

Example 1

<Production of Crystal of Compound 5A>

Using compound 1A as a starting material, a crystal of compound 5A was produced by the following steps. In the formulae, "BPMO" and "OMPB" each represents an O group linked to a BPM group. Also, "BPM" represents bromo(phenyl)methyl (also known as 4-bromobenzyl).

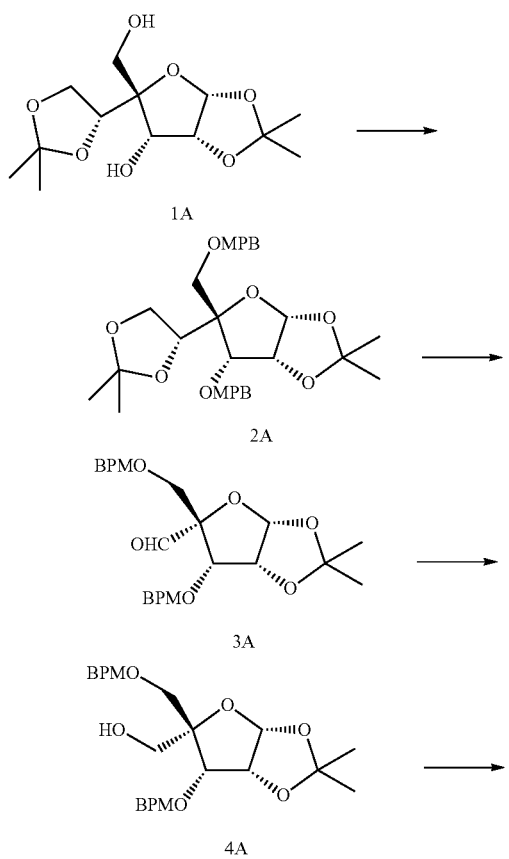

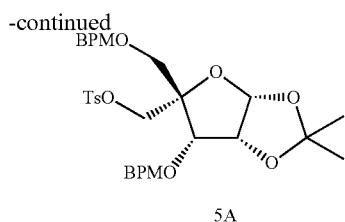

5A

Step of Obtaining Compound 2A (Compound Represented by Formula 2 in which $R^1$ is 4-Bromobenzyl Group) from Compound 1A Compound 1A (20.43 g, 70.37 mmol) was dissolved in dimethylacetamide (dehydrated, 352 mL) and cooled to 0° C. Sodium hydride (60% by mass, oil, 7.04 g, 0.176 mol) was added and stirred for 1 hour, and 4-bromobenzyl bromide (44.0 g, 0.176 mol) was then added and stirred at room temperature for 17 hours. Methanol (10 mL) was added to the reaction solution, stirred and then concentrated. To the resulting residue was added ethyl acetate and washed with water, and the organic phase was dried over anhydrous magnesium sulfate and concentrated to obtain compound 2A.

Step of Obtaining Compound 3A (Compound Represented by Formula 3 in which $R^1$ is 4-Bromobenzyl Group) from Compound 2A Compound 2A was dissolved in acetic acid (507 mL) by heating at 60° C., and 50 mL of an aqueous sodium periodate (30.1 g, 0.141 mol) solution (253 mL, dissolved by heating at 60° C.) was then added. After 5 minutes, 30 mL of the aqueous solution was added, and the remaining solution was then added over 5 minutes and stirred at the same temperature for 3 hours. The reaction solution was cooled to 0° C. and stirred for 45 minutes, and a precipitated solid (crystal) was then recovered by filtration. The solid was washed with acetic acid:deionized water (2:1 in a volume ratio), followed by deionized water, and then dried in vacuum to obtain a crystal of compound 3A (33.10 g, 59.51 mmol, 84.57%).

$^1$H-NMR (CDCl$_3$, 400 MHz); δ9.89 (1H, s), 7.48-7.44 (4H, m), 7.20-7.09 (4H, m), 5.86 (1H, d), 4.66 (1H, d), 4.63 (1H, t), 4.52 (1H, s), 4.47 (1H, d), 4.41 (1H, d), 4.31 (1H, d), 3.66 (1H, d), 3.60 (1H, d), 1.60 (3H, s), 1.36 (3H, s).

Step of Obtaining Compound 4A (Compound Represented by Formula 4 in which $R^1$ is 4-Bromobenzyl Group) from Compound 3A The crystal of compound 3A (33.10 g, 59.51 mmol) were suspended in methanol (298 mL) and tetrahydrofuran (298 mL) and cooled to 0° C. Sodium borohydride (563 mg, 14.9 mmol) was added by a small amount and stirred for 5 min, and the same amount of sodium borohydride (563 mg, 14.9 mmol) was then added and stirred for 2 hours. After concentrating the reaction solution to a small amount, ethyl acetate was added to the residue and washed with an aqueous saturated sodium hydrogen carbonate solution. The organic phase was dried over anhydrous magnesium sulfate and concentrated to obtain compound 4A.

Step of Obtaining Crystal of Compound 5A (Compound Represented by Formula 5 in which $R^1$ is 4-Bromobenzyl Group and $R^2$ is 4-Toluenesulfonyloxy Group) from Compound 4A After performing azeotrope of compound 4A with pyridine three times, the residue was dissolved in pyridine (dehydrated, 119 mL), and 4-toluenesulfonyl chloride (22.7 g, 0.119 mol) was added and stirred at 30° C. for 17 hours. Deionized water (10 mL) was added and stirred, and the reaction solution was then concentrated. To the residue was added ethyl acetate and washed with an aqueous saturated sodium hydrogen carbonate solution. The organic phase was dried over anhydrous magnesium sulfate and concentrated, and the residue was then subjected to azeotrope with toluene three times. The solidified residue was dissolved in ethyl acetate (50 mL), and hexane (100 mL) was added by a small amount (crystal precipitated). Hexane (100 mL) was further added and allowed to stand overnight. The precipitated solid was recovered by filtration, washed with hexane, and dried in vacuum to obtain a crystal of compound 5A (32.22 g, 45.20 mmol, 75.95%).

$^1$H-NMR (CDCl$_3$, 400 MHz); δ7.77 (2H, d), 7.45 (2H, d), 7.44 (2H, d), 7.29 (2H, d), 7.13 (2H, d), 7.08 (2H, d), 5.68 (1H, d), 4.63 (1H, d), 4.54 (1H, dd), 4.44 (1H, d), 4.43 (1H, d), 4.38 (1H, d), 4.32 (1H, d), 4.14 (1H, d), 3.51 (1H, d), 3.48 (1H, d), 2.42 (3H, s), 1.29 (3H, s), 1.27 (3H, s).

<Measurement of Physical Properties for Crystal of Compound 5A>

Physical properties shown in the following (1) to (4) were measured for the crystal of compound 5A obtained above.

(1) Microscopic Observation of Crystal Form

The crystal form of the crystal of compound 5A was observed using a digital microscope. The digital microscope used herein was Dino-Lite AD-4113 ZT (from AnMo Electronics Corporation), at magnifications of 230.

(2) Powder X-Ray Analysis

The crystal of compound 5A was subjected to powder X-ray analysis. A powder X-ray analyzer used herein was manufactured by Spectris, and analysis conditions were as follows:

[X-ray analyzer] X' Pert PRO MPD (Spectris);
[Target] Cu;
[X-ray tube current] 40 mA;
[X-ray tube voltage] 45 kV;
[Scanning range] 2θ=4.0 to 40°.

Figure 2:
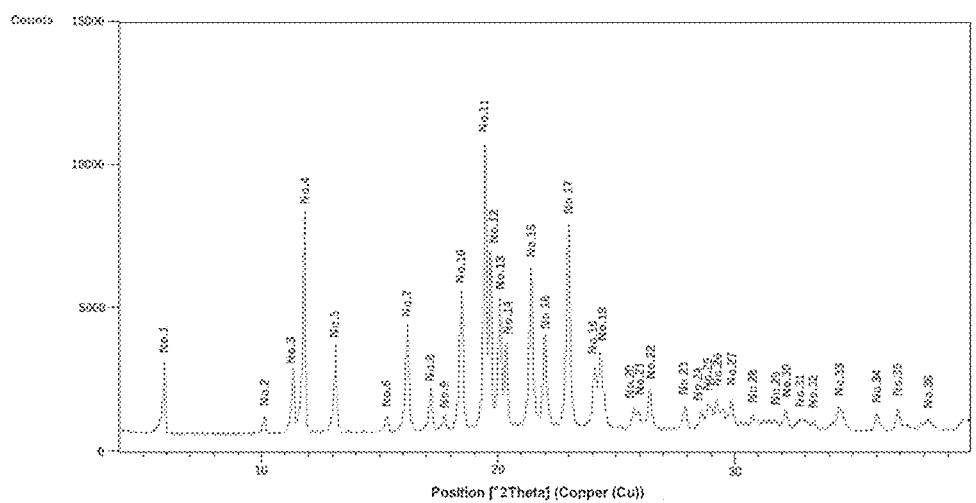
FIG. 2 shows a powder X-ray diffraction spectrum of a crystal of a compound represented by formula 5.

The measured results re shown in FIG. 2.

Compound 5A showed characteristic peaks near the diffraction angle (2θ) as shown in FIG. 2.

(3) Thermogravimetry/Differential Thermal Analysis (TG/DTA)

The crystal of compound 5A was subjected to thermogravimetry/differential thermal analysis (TG/DTA). The thermogravimetry/differential thermal analysis (TG/DTA) apparatus used herein was a thermal analyzer STA 7200 (from Hitachi High-Tech Science Corporation), and analysis conditions were as follows: Analysis conditions: the temperature was increased by 5° C. per minute in the range of from 30 to 190° C., and a change of heat quantity of a sample was measured. Aluminum oxide was used as a reference.

Figure 3:
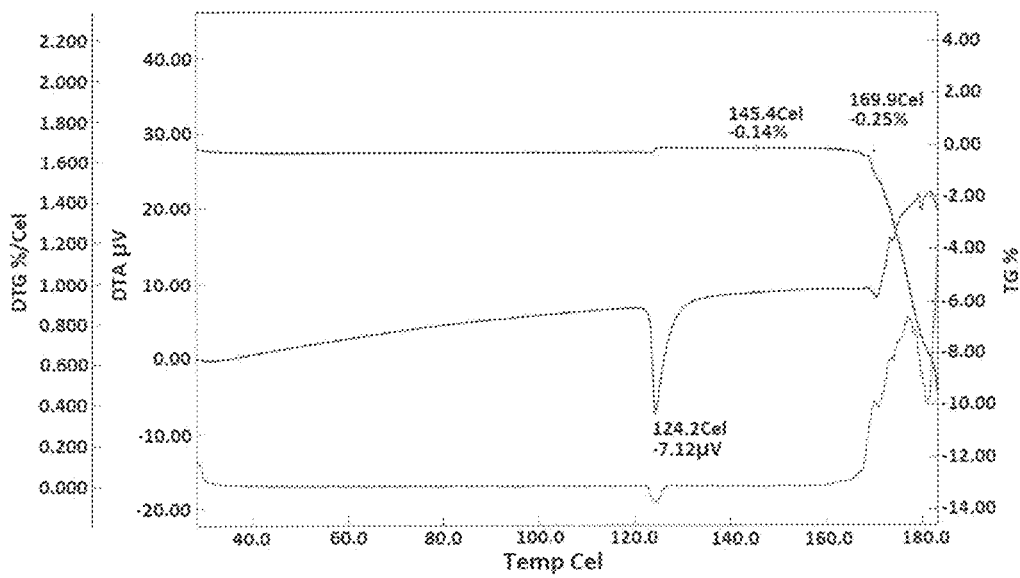
FIG. 3 shows e results of thermogravimetry/differential thermal analysis of a crystal of a compound represented by formula 5.

The measured results are shown in FIG. 3.

The crystal of compound 5A showed an endothermic peak at 124° C.

(4) Accelerated Stability Test

The crystal of compound 5A was subjected to an accelerated stability test.

The conditions for the accelerated test were as follows:

50 mg of the crystal of compound 5A was sampled in a glass sample bottle and heated at 80° C. for 7 days. One mg of the sample was dissolved in 1 mL of 5 mM triethylammonium acetate/70 vol % acetonitrile, and the purity was measured by high-performance liquid chromatography.

As a control, a solution of compound 5A in acetonitrile was also subjected to the accelerated test under the same conditions. 10 mg of the crystal of compound 5A was dissolved in 1 mL of acetonitrile and heated at 80° C. for 7 days. The sample solution was diluted 10 times with 5 mM triethylammonium acetate/70 vol % acetonitrile, and the purity was measured by high performance liquid chromatography.

The results are shown in FIG. 4.

The purity of compound 5A was decreased to 35% in the solution state under heating conditions at 80° C. for 7 days, while substantially no decomposition occurred in the crystalline state.

This indicates that compound 5A can be stably stored for a long period of time without special management as long as it is stored in the crystalline state. On the other hand, it is found that even with compound 5A, the intermediate cannot be stably stored for a long period of time in the solution state, as in the existing synthesis methods for crosslinked nucleoside intermediates.

<Comparison of Step 2 of Present Disclosure with Step Described in Non-Patent Literature 3>

Properties of the crystal of compound 3A obtained by the above method were compared with those of a solution of the compound represented by formula c synthesized under the conditions described in Non-Patent Literature 3.

Step of Obtaining Compound of Formula c from Compound of Formula b

The compound represented by formula c was produced from the compound represented by formula b according to the method described in Non-Patent Literature 3.

TLC was used to confirm the amount of impurities produced. Conditions for TLC were as follows:

TLC plate: Merck TLC Silica gel 60 F254; and

Development solvent: Hexane:Ethyl acetate=2:1 (volume ratio).

The results of TLC for the crystal of compound 3A are shown in FIG. 5(a), and the results of TLC for the solution of the compound represented by formula c described in Non-Patent Literature 3 is shown in FIG. 5(b).

It was confirmed that the synthesis of compound 3A by the above method caused the target crystal to be precipitated as the reaction progressed, and only filtration of the crystal provided compound 3A having higher purity without any chromatography operation.

In contrast, in the reaction mixture of the compound represented by formula c synthesized under the conditions described in Non-Patent Literature 3, the formation of byproducts was observed in addition to the compound represented by formula c. It was revealed that a chromatography operation was required for further purification to remove the byproducts, because the compound represented by formula c was amorphous.

Example 2

Using compound 5A produced in Example 1 as a raw material, various crosslinked nucleoside amidites of thymine, adenine, 5-methylcytosine, and guanine were produced.

(Example 2-1) Production of Thymine-Crosslinked Nucleoside Amidite

Thymine-crosslinked nucleoside amidite 11T was synthesized from compound 5A.

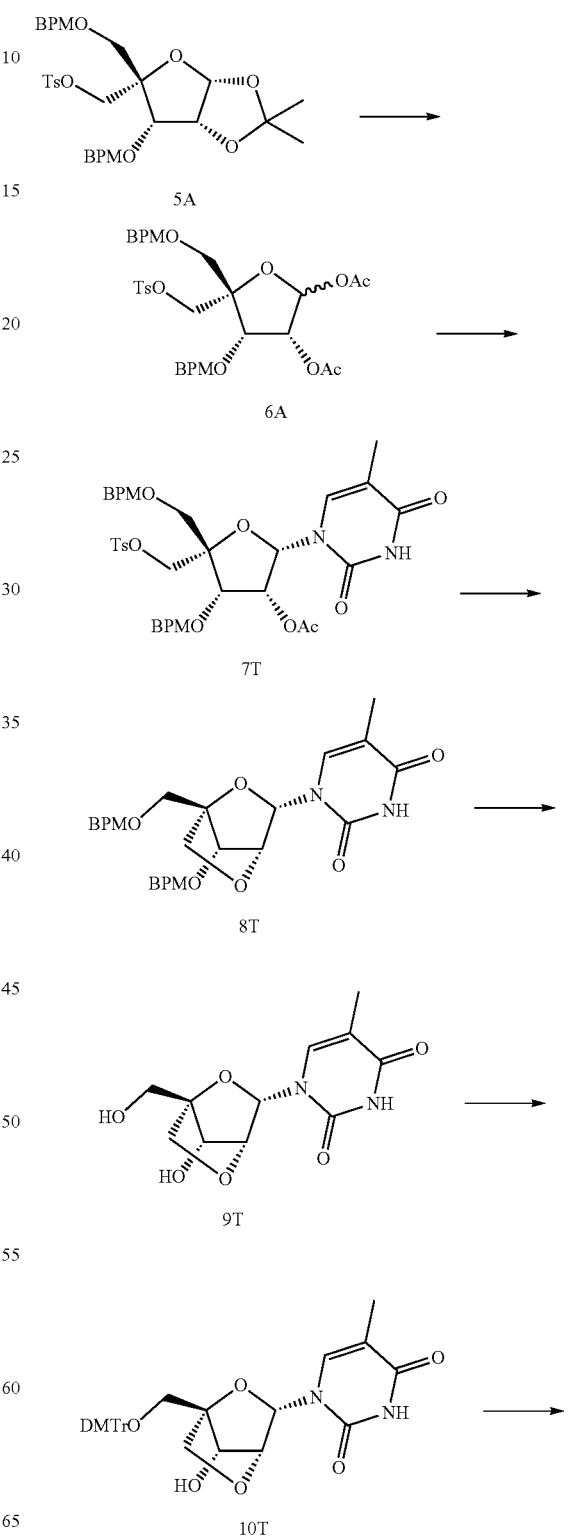

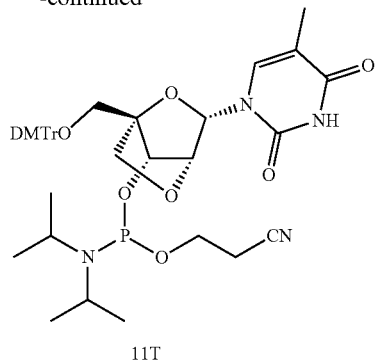

11T

Steps of Obtaining Compound 6A (Compound Represented by Formula 6 in which $R^1$ is 4-Bromobenzyl Group, and $R^2$ is 4-Toluenesulfonyloxy Group) from Compound 5A Compound 5A (33.10 g, 59.51 mmol) was suspended in acetic acid (366 mL), acetic anhydride (45.0 mL), and a solution of sulfuric acid (0.393 mL) in acetic acid (30.0 mL) was added and stirred at room temperature for 2 hours. Sodium acetate (1.50 g) was added to the reaction solution, stirred, and concentrated, and the residue was subjected to azeotrope with toluene five times. Ethyl acetate was added to the residue, and washed with an aqueous saturated sodium hydrogen carbonate solution. The resulting organic phase was dried over anhydrous magnesium sulfate and concentrated to obtain compound 6A.

Step of Obtaining Compound 7T (Compound Represented by Formula 7 in which $R^1$ is 4-Bromobenzyl Group, $R^2$ is 4-Toluenesulfonyloxy Group, and Base is Thymine) from Compound 6A To compound 6A, thymine (7.96 g, 63.1 mmol) and N,O-bis(trimethylsilyl)acetamide (33.9 mL, 0.139 mol) was added acetonitrile (105 mL) and stirred at 85° C. for 1 hour. After cooling the reaction solution to 0° C., trimethylsilyl trifluoromethanesulfonate (9.89 mL, 54.7 mmol) was added and stirred at 85° C. for 4 hours. After cooling the reaction solution to 0° C., an aqueous saturated sodium hydrogen carbonate solution was added and stirred. The precipitated solid was removed by filtration through celite, and then extracted with ethyl acetate (the ethyl acetate phase can be washed with an aqueous 1 M sodium hydroxide solution, then an aqueous saturated ammonium chloride solution, to remove residual thymine). The organic phase was dried over anhydrous magnesium sulfate and concentrated to obtain compound 7T.

Step of Obtaining Compound 8T (Compound Represented by Formula 8 in which $R^1$ is 4-Bromobenzyl Group, and Base is Thymine) from Compound 7T Methanol (211 mL) was added to compound 7T, and sodium hydroxide (8.42 g, 0.211 mol) was added and stirred at 40° C. for 3 hours. An aqueous saturated ammonium chloride solution was added to the reaction solution and extracted with ethyl acetate. The organic phase was dried over anhydrous magnesium sulfate and concentrated, and ethanol (150 mL) was then added to the residue, and ethyl acetate was added until it was dissolved. Under reduced pressure, ethyl acetate was distilled off, and the precipitated solid was recovered by filtration and washed with ethanol. The resulting solid was dried in vacuum to obtain compound 8T (20.00 g, 32.88 mmol, 78.1%).

$^1$H-NMR (CDCl$_3$, 400 MHz); δ8.39 (1H, s), 7.49 (2H, d), 7.46 (2H, d), 7.46 (1H, d), 7.18 (2H, d), 7.14 (2H, d), 5.64 (1H, s), 4.62-4.45 (5H, m), 4.02-3.78 (5H, m), 1.70 (3H, d).

Step of Obtaining Compound 9T (Compound Represented by Formula 9 in which Base is Thymine) from Compound 8T Compound 8T (7.13 g, 11.7 mmol) and ammonium formate (7.56 g, 0.12 mol) were dissolved in methanol (120 mL) and ethyl acetate (120 mL), and 20% by mass of palladium hydroxide/activated carbon (20% by mass of Pd, 50% by mass of water contained) (3.57 g) was added and stirred at 60° C. for 4 hours. After removing the catalyst by filtration through celite, the filtrate was concentrated and purified by silica gel column chromatography (150 mL of silica gel, chloroform:methanol=10:1 (volume ratio)) to obtain compound 9T (3.22 g, 11.9 mmol, 102%).

$^1$H-NMR (D$_2$O, 400 MHz); δ7.66 (1H, s), 5.67 (1H, s), 4.49 (1H, s), 4.22 (1H, s), 4.05-4.03 (3H, m), 3.96 (1H, d), 1.91 (3H, s).

Step of Obtaining Compound 10T from Compound 9T

Compound 9T (4.23 g, 15.7 mmol) was dissolved in pyridine (dehydrated, 52.3 mL), and dimethoxytrityl chloride (7.45 g, 22.0 mmol) was added and stirred at room temperature for 4 hours. Methanol (5 mL) was added to the reaction solution, stirred, and then concentrated. Ethyl acetate was added to the residue, and washed with an aqueous saturated sodium hydrogen carbonate solution, and the organic phase was then dried over anhydrous magnesium sulfate and concentrated. The residue was subjected to azeotrope with toluene three times and purified by silica gel column chromatography (250 mL of silica gel, hexane:ethyl acetate=1:1 to 1:2 (volume ratio)~ethyl acetate) to obtain compound 10T (8.99 g, 15.7 mmol, 100%).

$^1$H-NMR (CDCl$_3$, 400 MHz); δ8.54 (1H, s), 7.65-6.84 (14H, m), 5.63 (1H, s), 4.43 (1H, s), 4.28 (1H, d), 3.88 (2H, d), 3.81 (2H, d), 3.80 (6H, s), 3.58 (2H, d), 3.47 (2H, d), 2.31 (1H, d), 1.70 (3H, s).

Step of Obtaining Compound 11T from Compound 10T

Compound 10T (4.50 g, 7.86 mmol) and N,N-diisopropylethylamine (3.86 mL, 17.3 mmol) were dissolved in dichloromethane (dehydrated, 39.3 mL) and cooled to 0° C., to which 2-cyanoethyl diisopropylchlorophosphoramidide (3.86 mL, 17.3 mmol) was added and stirred at room temperature for 1 hour. The reaction solution was washed with an aqueous saturated sodium hydrogen carbonate solution, and the organic phase was then dried over anhydrous magnesium sulfate and concentrated. The residue was purified by silica gel column chromatography (200 ml of silica gel, hexane:ethyl acetate=1:1 (volume ratio)) to obtain compound 11T (6.00 g, 7.76 mmol, 98.7%).

$^{31}$P-NMR (CDCl$_3$, 160 MHz); δ149.94, 149.80.

(Example 2-2) Production of Adenine-Crosslinked Nucleoside Amidite

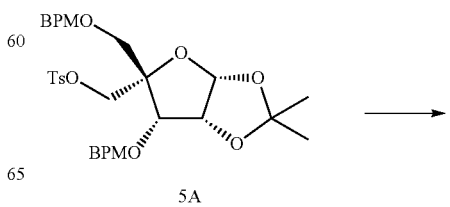

5A

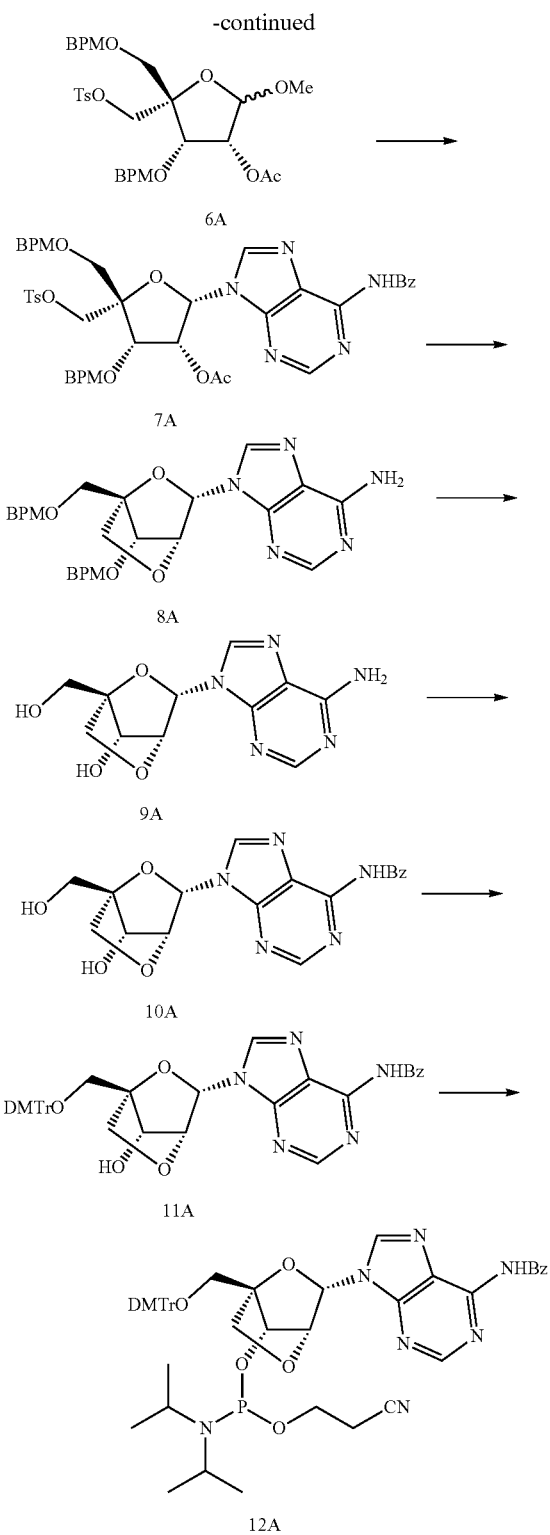

Step of Obtaining Compound 6A (Compound Represented by Formula 6 in which $R^1$ is 4-Bromobenzyl Group, and $R^2$ is 4-Toluenesulfonyloxy Group) from Compound 5A Compound 5A (24.0 g, 33.7 mmol) was suspended in acetic acid (340 mL, 0.1 mol/L), and acetic anhydride (35 mL, 262 mmol) and an acetic acid solution (371 mL) of sulfuric acid (0.32 mL, 6.07 mmol) were added sequentially with stirring at room temperature, and the mixture was stirred for 3 hours at the same temperature. At the end of the reaction, sodium acetate (1.2 g, 14.5 mmol) was added at the same temperature, stirred at the same temperature for 5 minutes and then concentrated. The residue was subjected to azeotrope with toluene (340 mL) three times. The resulting residue was dissolved in ethyl acetate (400 mL), and then washed with aqueous saturated sodium bicarbonate (100 mL) three times. After extracting the aqueous phase with ethyl acetate (400 mL) once, all the resulting organic phases were combined together, and dried over magnesium sulfate, and the solvent was distilled off under reduced pressure to obtain compound 6A.

Step of Obtaining Compound 7A (Compound Represented by Formula 7 in which $R^1$ is 4-Bromobenzyl Group, $R^2$ is 4-Toluenesulfonyloxy Group, and Base is $N^6$-Benzoyladenine) from Compound 6A To compound 6A, $N^6$-benzoyladenine (12.1 g, 50.6 mmol) was added toluene (85 mL, 0.4 mol/L), and then N,O-bis(trimethylsilyl)acetamide (25 mL, 101 mmol) was added with stirring at room temperature, and stirred under heat reflux for 1 hour. Subsequently, the temperature was lowered to 0° C., and trimethylsilyl trifluoromethanesulfonate (7.9 mL, 43.8 mmol) was then added at the same temperature, and stirred under heated reflux for 2 hours. At the end of the reaction, ethyl acetate (300 mL) and an aqueous 1 mol/L sodium hydroxide solution (100 mL) were added at 0° C., and stirred at the same temperature for 5 minutes. Subsequently, the precipitated solid was removed by filtration, and the organic phase was then separated from the aqueous phase. The resulting organic phase was washed three times with an aqueous 1 mol/L sodium hydroxide solution (50 mL), and then dried over magnesium sulfate and the solvent was then distilled off under reduced pressure to obtain compound 7A.

Step of Obtaining Compound 8A (Compound Represented by Formula 8 in which $R^1$ is 4-Bromobenzyl Group, and Base is Adenine) from Compound 7A To compound 7A were added methanol:tetrahydrofuran (9:1 (volume ratio), 170 ml), then sodium hydroxide (6.7 g, 169 mmol), and stirred at 40° C. for 1 hour. At the end of the reaction, an aqueous saturated ammonium chloride solution (170 mL) was added at the same temperature, and stirred at the same temperature for 5 minutes. Subsequently, ethyl acetate (200 mL) was added and stirred, and the precipitated solid was then removed by filtration. After concentrating the filtrate, the residue was dissolved in ethyl acetate (400 mL), and the organic phase was then separated from the aqueous phase. The resulting organic phase was washed once with deionized water (100 mL) and dried over magnesium sulfate, and the solvent was then distilled off under reduced pressure. To the resulting residue was added methanol (67 mL, 0.5 mol/L), and the residue was completely dissolved by stirring it under heat reflux. The temperature was then lowered to room temperature, and the precipitated crystal was collected by stirring the mixture overnight. The resulting crystal was washed twice with methanol (20 mL) to obtain compound 8A (14.3 g, 23.2 mmol, 68.7%).

$^1$H-NMR (CDCl$_3$, 400 MHz); δ8.33 (1H, s), 7.99 (1H, s), 7.47 (2H, d), 7.41 (2H, d), 7.18 (2H, d), 7.10 (2H, d), 6.03 (1H, s), 5.63 (2H, brs), 4.87 (1H, s), 4.58 (1H, d), 4.57 (2H, dd), 4.48 (1H, d), 4.26 (1H, s), 4.11 (1H, d), 3.99 (1H, d), 3.81 (2H, dd).

Step of Obtaining Compound 9A (Compound Represented by Formula 9 in which Base is Adenine) from Compound 8A To compound 8A (14.3 g, 23.2 mmol) were added ethyl acetate:methanol (1:3 (volume ratio), 600 mL), then ammonium formate (21.9 g, 348 mmol) and deionized water (37 mL), and stirred at 60° C. until it was dissolved. Subsequently, palladium hydroxide/activated carbon (2.9 g) was added at room temperature and stirred at 60° C. for 17 hours. Subsequently, ammonium formate (7.3 g, 116 mmol) and palladium hydroxide/activated carbon (0.7 g) were added, and stirred at 60° C. for 24 hours. At the end of the reaction, the catalyst was removed by filtration through celite, and the solvent was removed under reduced pressure to obtain compound 9A.

Step of Obtaining Compound 10A (Compound Represented by Formula 10 in which Base ($R^3$) is $N^6$-Benzoyladenine) from Compound 9A To compound 9A, which had undergone azeotropic dehydration (100 mL of pyridine, three times), were added pyridine (116 mL, 0.2 mol/L), and then chlorotrimethylsilane (20.6 mL, 162 mmol) at 0° C., and stirred at the same temperature for 30 minutes. Subsequently, benzoyl chloride (13.5 mL, 116 mmol) was added at the same temperature, and stirred for 21 hours. Subsequently, methanol (116 mL) was added, and stirred at room temperature for 5 minutes, and ammonia water (34 mL) was then added and stirred at the same temperature for 2.5 hours. The end of the reaction, the solid that had precipitated was removed by filtration, and the solvent was distilled off under reduced pressure. Subsequently, pyridine (100 mL) was added, and stirred for 5 minutes, and the solid that was not dissolved was then removed by filtration. The solvent was distilled off under reduced pressure to obtain compound 10A.

Step of Obtaining Compound 11A from Compound 10A

To compound 10A, which had undergone azeotropic dehydration (70 ml of pyridine, three times) were added pyridine (77 ml, 0.3 mol/L), and then dimethoxytrityl chloride (9.6 g, 28.2 mmol) with stirring at room temperature, and stirred at the same temperature for 1 hour. Subsequently, dimethoxytrityl chloride (11.8 g, 34.8 mmol) was added, and stirred for 12 hours. At the end of the reaction, methanol (80 mL) was added, and stirred at the same temperature for 5 minutes, and the solvent was then distilled off under reduced pressure. The resulting residue was dissolved in ethyl acetate (320 mL), and then washed once with deionized water (80 mL). After performing drying over magnesium sulfate and removal of the solvent under reduced pressure in this order, the product was purified by medium-pressure silica gel column chromatography (100 g of $SiO_2$, ethyl acetate: hexane=66:34 (volume ratio)~ethyl acetate) to obtain compound 11A (9.41 g, 13.7 mmol, 59.1%).

$^1$H-NMR (CDCl$_3$, 400 MHz); δ9.10 (1H, s), 8.77 (1H, s), 8.28 (1H, s), 8.02 (2H, d), 7.63-7.21 (12H, m), 6.85 (4H, d), 6.13 (1H, s), 4.44 (1H, d), 4.04 (2H, s), 3.61 (1H, d), 3.56 (1H, d), 2.65 (1H, d).

Step of Obtaining Compound 12A from Compound 11A

To compound 11A (9.41 g, 13.7 mmol) azeotropically dehydrated (with 70 mL toluene, three times) were sequentially added dichloromethane (70 mL) and N,N-diisopropylethylamine (6.0 mL, 34.3 mmol), and then (2-cyanoethyl)(N,N-diisopropyl)chlorophosphoramidite (6.7 mL, 30.1 mmol) with stirring at 0° C., and the mixture was stirred at room temperature for 2.5 hours. At the end of the reaction, aqueous saturated sodium bicarbonate (50 mL) was added at 0° C., and stirred at the same temperature for 5 minutes, and then the organic and aqueous phases were separated. After extracting the aqueous phase once with ethyl acetate (70 mL), all the resulting organic phases were combined together, and dried over magnesium sulfate, and the solvent was distilled off under reduced pressure. Subsequently, the product was purified by medium-pressure silica gel column chromatography (100 g of $SiO_2$, ethyl acetate:hexane=69:31 to 90:10 (volume ratio)) to obtain compound 12A (9.4 g, 10.6 mmol, 77.0%).

$^{31}$P-NMR (MeCN-d$_3$, 160 MHz); δ149.54, 149.04.

(Example 2-3) Production of 5-Methylcytosine-Crosslinked Nucleoside Amidite

5-Methylcytosine-crosslinked nucleoside amidite 12C was synthesized from compound 5A.

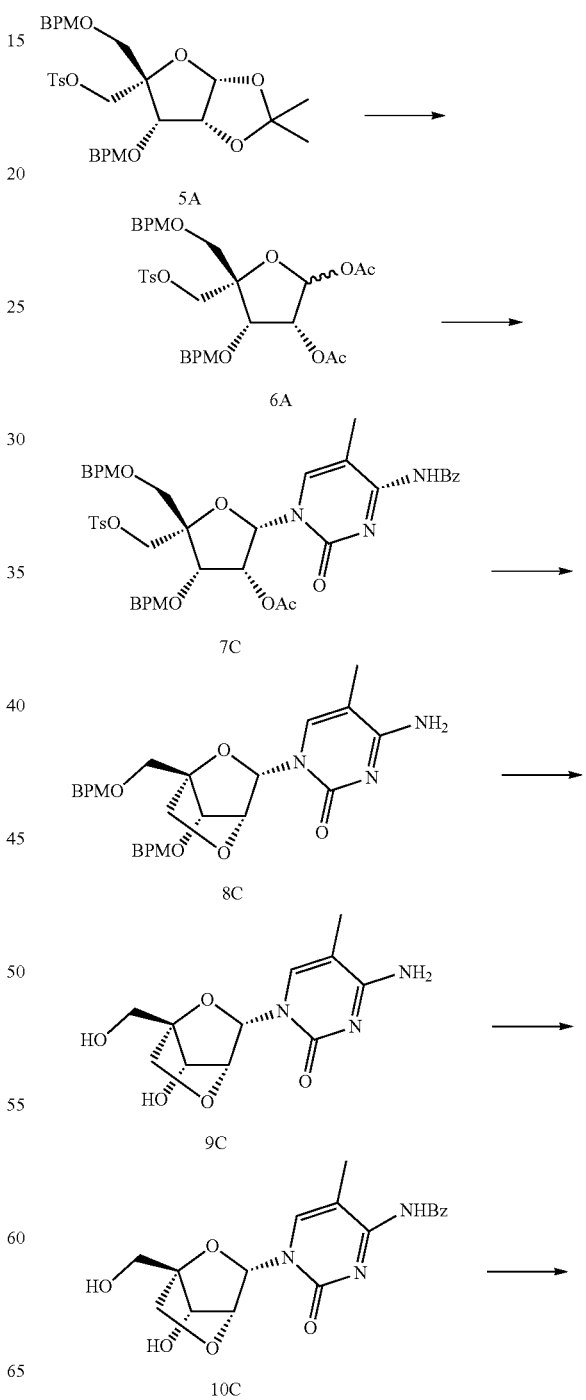

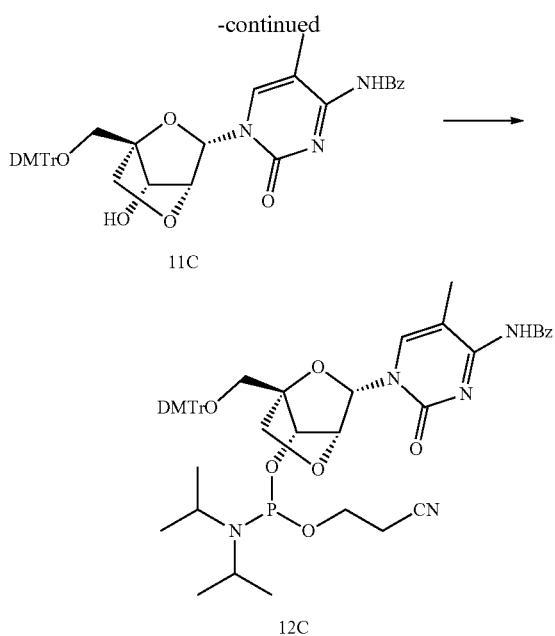

Step of Obtaining Compound 6A (Compound Represented by Formula 6 in which $R^1$ is 4-Bromobenzyl Group, and $R^2$ is 4-Toluenesulfonyloxy Group) from Compound 5A Compound 5A (30.0 g, 42.1 mmol) was suspended in acetic acid (366 mL) and acetic anhydride (45.0 mL), and a solution of concentrated sulfuric acid (396 μL) in acetic acid (30.0 mL) was slowly dropped, and then stirred at room temperature for 2 hours. Sodium acetate (1.50 g, 18.3 mmol) was added to the reaction solution and stirred until it was completely dissolved, and then concentrated. After the residue was subjected to azeotrope (40 mL×5) with toluene/ethyl acetate (2:1 in volume ratio), ethyl acetate (300 mL) was added to the residue and washed with an aqueous saturated sodium hydrogen carbonate solution (150 mL). The organic phase was dried over anhydrous magnesium sulfate and concentrated. The residue was subjected to azeotrope (20 mL×3) with toluene to obtain compound 6A.

A Step of Obtaining Compound 7C (Compound Represented by Formula 7 in which $R^1$ is 4-Bromobenzyl Group, $R^2$ is 4-Toluenesulfonyloxy Group, and Base is $N^4$-Benzoyl-5-Methylcytosine) from Compound 6A Compound 6A was dissolved in acetonitrile (super-dehydrated) (105 ml), to which $N^4$-benzoyl-5-methylcytosine (12.7 g, 55.4 mmol), and N,O-bis(trimethylsilyl)acetamide (29.8 mL, 0.122 mol) were added, and heated with stirring at 85° C. for 1 hour. After the reaction solution was ice-cooled, trimethylsilyl trifluoromethanesulfonate (11.4 mL, 63.1 mmol) was added, and heated with stirring at 85° C. for 8 hours. After the reaction solution was ice-cooled, an aqueous saturated aqueous sodium bicarbonate solution (150 mL) was added, and stirred until foaming was subsided. The reaction solution was extracted with ethyl acetate (150 mL), and the organic phase was dried over anhydrous magnesium sulfate and concentrated to obtain compound 7C.

Step of Obtaining Compound 8C (Compound Represented by Formula 8 in which $R^1$ is 4-Bromobenzyl Group, and Base is 5-Methylcytosine) from Compound 7C Compound 7C was dissolved in tetrahydrofuran (21 mL), and methanol (211 mL) and sodium hydroxide (8.42 g, 0.211 mol) were added, and heated with stirring at 40° C. for 14 hours. After concentrating the reaction solution to a small amount, it was diluted with ethyl acetate (200 mL) and washed with 1 mol/L hydrochloric acid (100 mL) and an aqueous saturated sodium hydrogen carbonate solution (100 mL). The organic phase was dried over anhydrous magnesium sulfate and then concentrated. The residue was dissolved in acetone (30 mL), and deionized water (15 mL) was added. Acetone was added until the solution became transparent, and then the precipitated solid was recovered by filtration. The solid was washed with 50% by volume of ethanol and then dried in vacuum to obtain compound 8C (18.71 g, 30.81 mmol, 73.17%).

$^1$H-NMR (CDCl$_3$, 400 MHz); δ8.54 (1H, s), 7.50-7.42 (5H, m), 7, 19-7.11 (4H, m), 5.71 (1H, s), 4.71 (1H, s), 4.60-4.52 (3H, m), 4.38 (1H, d), 4.00 (1H, d), 3.87-3.79 (4H, m), 3.71 (2H, s), 1.67 (3H, d).

Step of Obtaining Compound 9C (Compound Represented by Formula 9 in which Base is 5-Methylcytosine) from Compound 8C Compound 8C (16.07 g, 26.46 mmol) was dissolved in tetrahydrofuran (142 mL) and methanol (142 mL), and ammonium formate (16.8 g, 0.266 mol) was added and dissolved. One mol/L hydrochloric acid (26.4 mL, 26.4 mmol) and palladium/active carbon (8.04 g) were added, and heated with stirring at 60° C. for 23 hours. Deionized water (27 mL) was added to dissolve the precipitate, and palladium hydroxide/activated carbon was then removed by filtration through celite and washed with 50% by volume of methanol (100 mL×5). The filtrate and washing solution were concentrated, and the residue was dissolved in deionized water (100 mL) and adsorbed on a Dowex 50W ×8 (H$^+$ type) column (60 mL). After washing the column with water, it was eluted with 0.2-0.5 mol/L ammonia water. The fraction containing the target product was concentrated and dried in vacuum to obtain compound 9C (6.83 g, 25.4 mmol, 96.0%).

$^1$H-NMR (D$_2$O, 400 MHz); δ7.62 (1H, s), 5.66 (1H, s), 4.46 (1H, s), 4.19 (1H, s), 4.04 (1H, d), 4.04 (2H, s), 3.96 (1H, d), 1.98 (3H, s).

Step of Obtaining Compound 10C (Compound Represented by Formula 10 in which Base ($R^3$) is $N^4$-Benzoyl-5-Methylcytosine) from Compound 9C Compound 9C (9.15 g, 34.0 mmol) was dissolved in pyridine (dehydrated) (118 mL), and benzoic anhydride (15.4 g, 68.1 mmol) was added, and stirred at room temperature for 3 days. Ethanol (116 mL) and an aqueous 2 mol/L sodium hydroxide solution (174 mL, 0.348 mol) were added to the reaction solution and stirred for 1 hour, and acetic acid (23 mL) was then added. After concentrating the reaction solution, the residue was subjected to azeotrope with deionized water twice. The residue was dissolved in deionized water (25 mL), and the precipitated solid was recovered by filtration and washed with water. The resulting solid was recrystallized from deionized water to obtain compound 10C (10.19 g, 27.29 mmol, 80.3%).

$^1$H-NMR (DMSO-d6, 400 MHz); δ8.15-7.45 (6H, m), 5.67 (1H, d), 5.46 (1H, s), 5.22 (1H, t), 4.17 (1H, s), 3.90 (1H, d), 3.83-3.63 (4H, m), 2.00 (3H, s).

Step of Obtaining Compound 11C from Compound 10C

Compound 10C (7.00 g, 18.7 mmol) was subjected to azeotrope with pyridine three times, and then dissolved in pyridine (dehydrated) (62.3 mL). Dimethoxytrityl chloride (8.24 g, 24.3 mmol) was added and stirred at room temperature for 2 hours, and methanol (5 mL) was then added to the reaction solution and concentrated. To the residue was added ethyl acetate (200 mL), and washed with an aqueous saturated sodium hydrogen carbonate solution (50 mL). The organic phase was dried over anhydrous magnesium sulfate and concentrated, and the residue was subjected to azeotrope with toluene (20 mL×3). The residue was purified by medium-pressure silica gel column chromatography (100 g of SiO$_2$, hexane:ethyl acetate=2:1 to 1:1 to 1:3 (volume ratio)) under the following conditions to obtain compound 11C (12.14 g, 18.00 mmol, 96.26%).

$^1$H-NMR (CDCl$_3$, 400 MHz); δ8.32 (2H, d), 7.83 (1H, s), 7.55-7.25 (12H, m), 6.89-6.85 (4H, m), 5.70 (1H, s), 4.47 (1H, s), 4.29 (1H, d), 3.85 (2H, dd), 3.81 (6H, s), 3.62 (1H, d), 3.48 (1H, d), 1.90 (3H, s), 1.86 (1H, d).

Step of Obtaining Compound 12C from Compound 11C

Compound 11C (11.50 g, 17.02 mmol) was dissolved in dichloromethane (super-dehydrated) (85.1 mL), and N,N-diisopropylethylamine (6.02 mmol, 35.2 mmol) and (2-cyanoethyl)(N,N-diisopropyl)chlorophosphoramidite (6.83 mL, 30.6 mmol) were added and stirred at room temperature for 2 hours. The reaction solution was diluted with chloroform (100 mL) and washed with an aqueous saturated sodium hydrogen carbonate solution/aqueous saturated sodium chloride solution (50 mL+50 mL). The organic phase was dried over anhydrous magnesium sulfate and concentrated. The residue was purified by medium-pressure silica gel column chromatography (100 g of SiO$_2$, hexane:ethyl acetate=3:1 to 2:1 to 1:1 (volume ratio)) under the following conditions to obtain compound 12C (10.70 g, 12.22 mmol, 71.80%).

$^{31}$P-NMR (CDCl$_3$, 160 MHz); δ150.10, 150.04.

(Example 2-4) Production of Guanine-Crosslinked Nucleoside Amidite

Guanine-crosslinked nucleoside amidite 13G was synthesized from compound 5A.

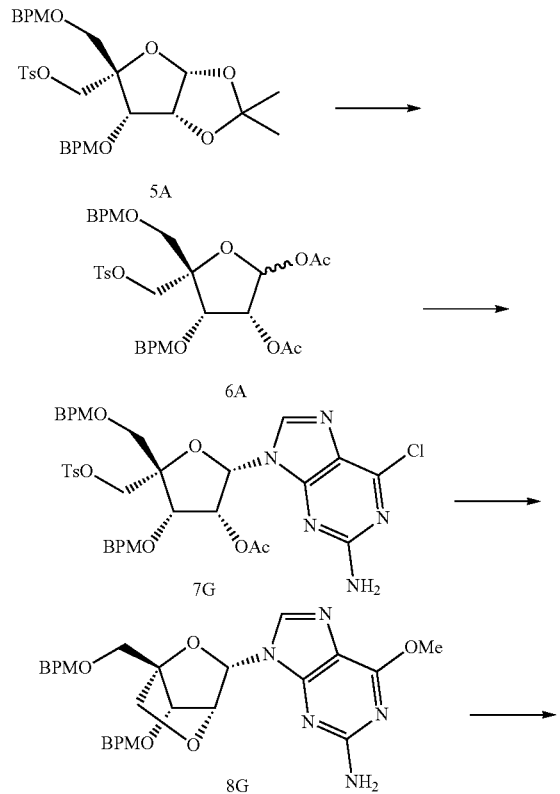
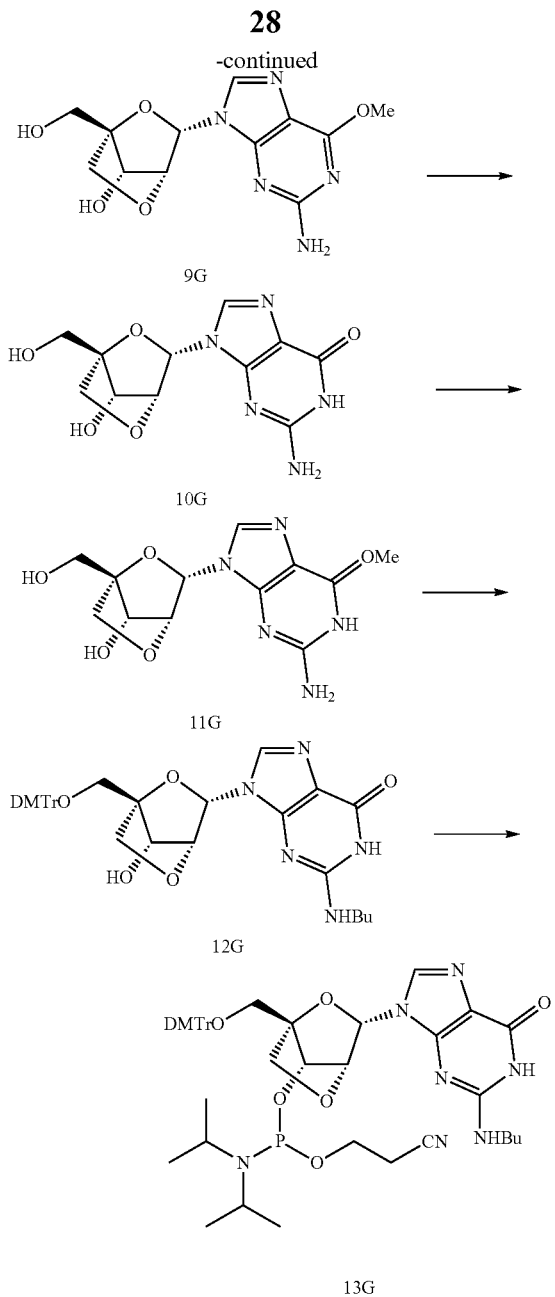

Step of Obtaining Compound 6A (Compound Represented by Formula 6 in which R$^1$ is 4-Bromobenzyl Group, and R$^2$ is 4-Toluenesulfonyloxy Group) from Compound 5A Compound 5A (30.0 g, 42.1 mmol) was suspended in acetic acid (366 mL) and acetic anhydride (45.0 mL), and a solution of concentrated sulfuric acid (396 μL) in acetic acid (30.0 mL) was slowly dropped, and then stirred at room temperature for 2 hours. Sodium acetate (1.50 g, 18.3 mmol) was added to the reaction solution and stirred until it was completely dissolved, and then concentrated. After the residue was subjected to azeotrope (40 mL×5) with toluene/ethyl acetate (2:1 in volume ratio), ethyl acetate (300 mL) was added to the residue and washed with an aqueous saturated sodium hydrogen carbonate solution (150 mL). The organic phase was dried over anhydrous magnesium sulfate and concentrated. The residue was subjected to azeotrope (20 mL×3) with toluene to obtain compound 6A.

Step of Obtaining Compound 7G (Compound Represented by Formula 7 in which $R^1$ is 4-Bromobenzyl Group, $R^2$ is 4-Toluenesulfonyloxy Group, and Base is 2-Amino-Chloropurine) from Compound 6A Compound 6A was dissolved in acetonitrile (super-dehydrated) (105 ml), and 2-amino-6-chloropurine (10.7 g, 63.1 mmol) and N,O-bis(trimethylsilyl)acetamide (33.9 mL, 0.137 mol) were added, and heated with stirring at 85° C. for 1 hour. After the reaction solution was ice-cooled, trimethylsilyl trifluoromethanesulfonate (15.2 mL, 84.1 mmol) was added, and heated with stirring at 85° C. for 7 hours. After the reaction solution was ice-cooled, an aqueous saturated sodium hydrogen carbonate solution was added and stirred until the foaming was stopped. The reaction solution was extracted with ethyl acetate (150 mL), and the organic phase was washed with an aqueous 1M sodium hydroxide solution, dried over anhydrous magnesium sulfate, and concentrated to obtain compound 7G.

Step of Obtaining Compound 8G (Compound Represented by Formula 8 in which $R^1$ is 4-Bromobenzyl Group, and Base is 2-Amino-6-Methoxypurine) from Compound 7G Compound 7G was dissolved in tetrahydrofuran (105 mL), and methanol (421 mL) and a 25 vol % sodium methoxide methanol solution (80.9 mL) were added, and heated with stirring at room temperature for 24 hours. The reaction mixture was neutralized with 2M hydrochloric acid and then concentrated. Ethyl acetate was added to the residue, and washed with an aqueous saturated sodium hydrogen carbonate solution. The organic phase was dried over anhydrous magnesium sulfate and then concentrated. The residue was dissolved in ethyl acetate, activated carbon (1.0 g) was added, and the mixture was heated with stirring at 60° C. for 1 hour. After removing the activated carbon by filtration through celite, the filtrate was concentrated to obtain compound 8G.

Step of Obtaining Compound 9G (Compound Represented by Formula 9 in which Base is 2-Amino-6-Methoxypurine) from Compound 8G Compound 8G was dissolved in tetrahydrofuran (213 mL) and methanol (213 mL), and ammonium formate (26.9 g, 0.427 mol) was added and dissolved. Palladium hydroxide/activated carbon (13.5 g) was added, and heated with stirring at 60° C. for 30 hours. Palladium hydroxide/activated carbon was removed by filtration through celite and washed with methanol (100 mL×5). After concentrating the filtrate and the washing solution, the residue was dissolved in deionized water (300 mL) and washed with toluene. The solution was passed through an IRA 93 (OH-type) column (150 mL), washed with water and concentrated to obtain compound 9G.

Step of Obtaining Compound 10G (Compound Represented by Formula 9 in which Base is Guanine) from Compound 9G Compound 9G was dissolved in 100 mM Tris-HCl (pH 7.5) (420 mL), adenosine deaminase (37 µL, 42 units) was added, and the mixture was stirred at 40° C. for 24 hours. Adenosine deaminase (37 µL, 42 units) was added and further stirred at the same temperature for 24 hours. The precipitated solid was collected by filtration, washed with water, and dried in vacuum to obtain compound 10G (8.50 g, 28.8 mmol, 68.4%).

$^1$H-NMR (DMSO-$d_6$, 400 MHz); δ10.63 (1H, s), 7.79 (1H, s), 6.56 (2H, s), 5.68-5.67 (2H, m), 5.03 (1H, t), 4.28 (1H, s), 4.14 (1H, d), 3.88 (1H, d), 3.77 (2H, m), 3.71 (1H, d).

Step of Obtaining Compound 11G (Compound Represented by Formula (10) in which Base ($R^3$) is $N^2$-Isobutyrylguanine) from Compound 10G Compound 10G (600 mg, 2.03 mmol) is dissolved in N,N-dimethylformamide (dehydrated) (4.1 mL), and tert-butylchlorodimethylsilane (1.22 g, 8.09 mmol) was added and stirred at room temperature for 20 hours. The reaction solution was diluted with ethyl acetate, and washed with water, and the organic phase was dried over anhydrous magnesium sulfate and concentrated. The residue was purified by silica gel column chromatography (100 mL of $SiO_2$, chloroform:methanol=20:1 (volume ratio)).

The residue was dissolved in pyridine (8.0 mL), and ice-cooled isobutyryl chloride (336 µL, 3.18 mmol) was added, and the mixture was stirred at room temperature for 20 hours. Deionized water was added and stirred, and the reaction solution was then concentrated. Ethyl acetate was added to the residue, washed with aqueous saturated sodium bicarbonate, and the organic phase was dried over anhydrous magnesium sulfate and concentrated. The residue was subjected to azeotrope with toluene three times, and the residue was purified by silica gel column chromatography (100 mL of $SiO_2$, chloroform:methanol=50:1 (volume ratio)).

The residue was dissolved in methanol (10.0 mL), acidic ammonium hydrogen fluoride (860 mg, 15.0 mmol) was added, and the mixture was heated with stirring at 60° C. for 17 hours. Silica gel was added to the reaction solution, and the solvent was distilled off and then purified by silica gel column chromatography (100 mL of $SiO_2$, chloroform:methanol=10:1 to 5:1 (volume ratio)) to obtain compound 11G (0.53 g, 1.5 mmol, 74%).

$^1$H-NMR (DMSO-$d_6$, 400 MHz); δ12.11 (1H, s), 11.77 (1H, s), 8.09 (1H, s), 5.80 (1H, s), 5.73 (1H, d), 5.06 (1H, t), 4.37 (1H, s), 4.15 (1H, d), 3.92-3.72 (4H, m), 2.77 (1H, m), 1.12 (6H, d).

Step of Obtaining Compound 12G from Compound 11G

Compound 11G (1.87 g, 5.12 mmol) was subjected to azeotrope with pyridine three times, and then dissolved in pyridine (dehydrated) (17.1 mL). Dimethoxytrityl chloride (2.43 g, 7.17 mmol) was added and stirred at room temperature for 2 hours, and then methanol (1 mL) was added to the reaction solution and concentrated. To the residue was added ethyl acetate (200 mL), and washed with an aqueous saturated sodium hydrogen carbonate solution. The organic phase was dried over anhydrous magnesium sulfate and then concentrated, and the residue was subjected to azeotrope with toluene (20 mL×3). The residue was purified by silica gel column chromatography (150 g of $SiO_2$, hexane: ethyl acetate=1:1 to 1:3 (volume ratio)~ethyl acetate) to obtain compound 12G (3.27 g, 4.90 mmol, 95.7%).

$^1$H-NMR (DMSO-$d_6$, 400 MHz); δ12.05 (1H, s), 8.93 (1H, s), 7.88 (1H, s), 7.44-7.13 (9H, m), 6.79 (4H, m), 5.78 (1H, s), 4.60 (1H, s), 4.44 (1H, s), 4.05 (1H, d), 3.99 (1H, d), 3.74 (3H, s), 3.74 (3H, s), 3.61 (1H, d), 3.55 (1H, d), 2.64 (1H, m), 1.24 (3H, d), 1.23 (3H, d).

Step of Obtaining Compound 13G from Compound 12G

Compound 12G (3.20 g, 4.79 mmol) was dissolved in dichloromethane (super-dehydrated) (24.0 mL), and N,N-diisopropylethylamine (2.03 mL, 11.9 mmol) and (2-cyanoethyl)(N, N-diisopropyl)chlorophosphoroamidite (2.35 mL, 10.5 mmol) were added, and stirred at room temperature for 3 hours. The reaction solution was washed with an aqueous saturated sodium hydrogen carbonate solution. The organic phase was dried over anhydrous magnesium sulfate and then concentrated. The residue was purified by silica gel column chromatography (200 g of SiO$_2$, hexane:ethyl acetate=1:1 to 1:2 (volume ratio)) to obtain compound 13G (3.36 g, 3.87 mmol, 80.8%).

$^{31}$P-NMR (MeCN-d$_3$, 160 MHz); δ149.09, 148.74.

The invention claimed is:

1. A crystal of a compound represented by the following formula 5:

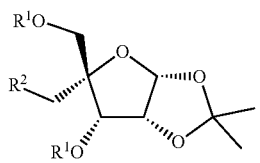

5 in which R$^1$ represents a protecting group for a hydroxyl group, and R$^2$ represents a leaving group.

2. The crystal according to claim 1, wherein the crystal shows peaks at 5.9±0.3, 11.4±0.6, 11.8±0.6, 13.2±0.7, 16.2±0.8, 17.2±0.9, 18.5±0.9, 19.5±1.0, 19.7±1.0, 20.1±1.0, 20.4±1.0, 21.4±1.1, 22.0±1.1, 23.0±1.2, 24.1±1.2, 24.3±1.2, 26.4±1.3, and 29.9±1.5(°) as a diffraction angle (2θ) in powder X-ray analysis.

3. The crystal according to claim 1, wherein the crystal shows an endothermic peak at 124° C. as measured by a thermogravimetry/differential thermal analysis (TG/DTA) apparatus.

4. The crystal according to claim 1, wherein the compound represented by the formula 5 is a crosslinked nucleoside intermediate.

5. A method for producing a crystal of a compound represented by formula 5, the method comprising the following steps 1 to 5:
   step 1: protecting hydroxyl groups of a compound represented by formula 1 to obtain a compound represented by formula 2;
   step 2: converting a dimethyldioxolanyl group at position 4 of a compound represented by formula 2 to an aldehyde group to obtain a compound represented by formula 3;
   step 3: reducing the compound represented by the formula 3 to convert the aldehyde group at the position 4 to a hydroxyl group to obtain a compound represented by formula 4;
   step 4: converting the hydroxyl group at the position 4 of the compound represented by the formula 4 to a leaving group to obtain a compound represented by formula 5; and
   step 5: crystallizing the compound represented by the formula 5 from a crystallization solvent to obtain the crystal of the compound represented by the formula 5;

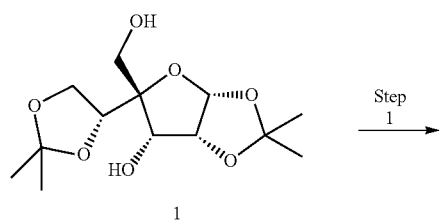

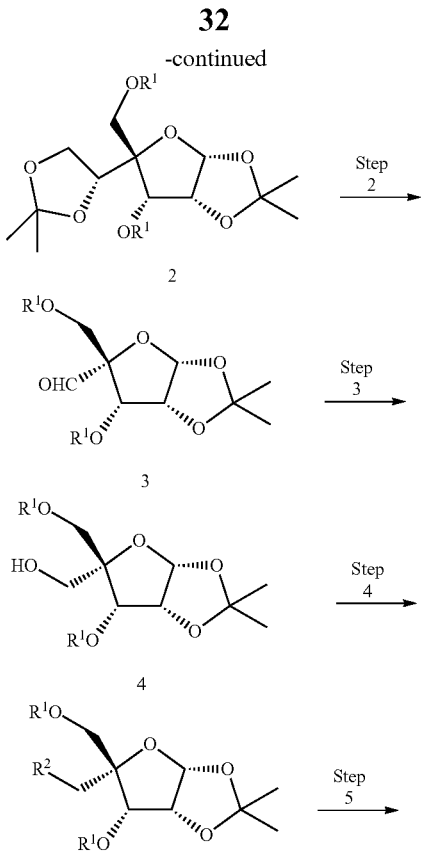

Crystal of Compound of Formula 5 in which R$^1$ represents a protecting group for a hydroxyl group, and R$^2$ represents a leaving group.

6. The method for producing the crystal according to claim 5, further comprising a crystallization step between the step 2 and the step 3.

7. The method for producing the crystal according to claim 5, wherein the compound represented by the formula 5 is a crosslinked nucleoside intermediate.

8. A method for producing a crosslinked nucleoside amidite, the method comprising the following steps:
   step 6: suspending the crystal of the compound represented by the formula 5 obtained by the method according to claim 5 in a solvent, and then converting isopropylidene groups of the compound to acetyl groups to obtain a compound represented by formula 6;
   step 7: condensing the compound represented by the formula 6 with a silylated base to obtain a compound represented by formula 7;
   step 8: removing protecting groups of the compound represented by the formula 7 while at the same time performing a cyclization reaction to obtain a compound represented by formula 8;
   step 9: removing the protecting groups for the hydroxyl groups of the compound represented by the formula 8 to obtain a compound represented by formula 9; and
   step 10: optionally introducing a protecting group into the amino group on the base moiety of the compound represented by the formula 9 to obtain a compound represented by formula 10;

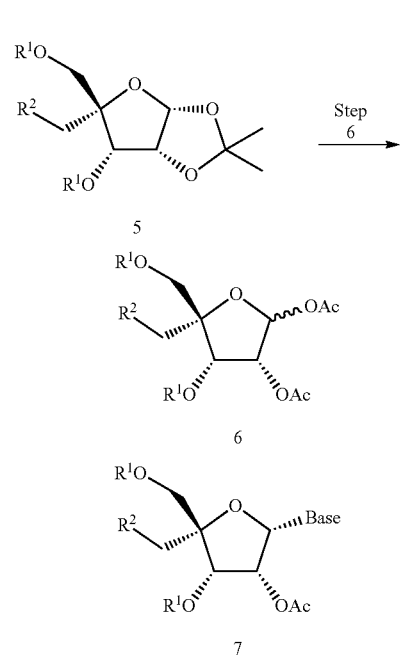
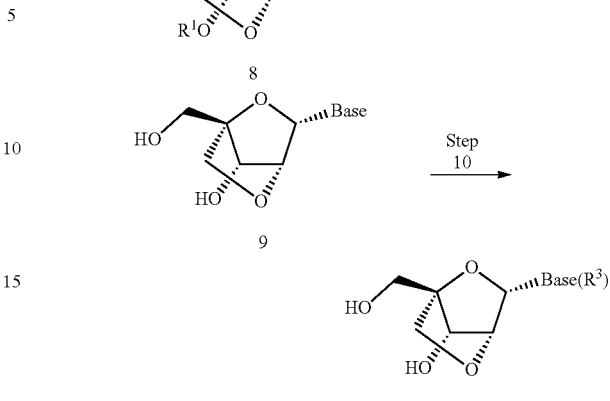
in which R[1] represents a protecting group for the hydroxyl group, R[2] represents a leaving group, and R[3] represents a hydrogen atom or an amino-protecting group.
\* \* \* \* \*